US012788915B2

(12) United States Patent
Dodd et al.

(10) Patent No.: US 12,788,915 B2
(45) Date of Patent: Nov. 10, 2026

(54) SYSTEMS AND METHODS FOR COMMUNICATING AN INDICATION OF A SLEEP-RELATED EVENT TO A USER

(71) Applicant: ResMed Sensor Technologies Limited, Dublin (IE)

(72) Inventors: Stephen Dodd, Dublin (IE); Roxana Tiron, Dublin (IE); Michael John Costello, Dublin (IE); Kieran Conway, Dublin (IE)

(73) Assignee: RedMed Sensor Technologies Limited, Dublin (IE)

( * ) Notice: Subject to any disclaimer, the term of this patent is extended or adjusted under 35 U.S.C. 154(b) by 798 days.

(21) Appl. No.: 18/011,272

(22) PCT Filed: Jun. 25, 2021

(86) PCT No.: PCT/IB2021/055714
§ 371 (c)(1),
(2) Date: Dec. 19, 2022

(87) PCT Pub. No.: WO2021/260656
PCT Pub. Date: Dec. 30, 2021

(65) Prior Publication Data

US 2023/0248927 A1 Aug. 10, 2023

Related U.S. Application Data

(60) Provisional application No. 63/044,760, filed on Jun. 26, 2020.

(51) Int. Cl.
*A61M 16/00* (2006.01)
*G06F 3/16* (2006.01)

(52) U.S. Cl.
CPC ........... *A61M 16/021* (2017.08); *G06F 3/165* (2013.01); *A61M 2205/3375* (2013.01); *A61M 2205/505* (2013.01); *A61M 2230/42* (2013.01)

(58) Field of Classification Search
CPC ... A61B 5/0816; A61B 5/4815; A61B 5/4818; A61B 5/4836; A61B 5/743;
(Continued)

(56) References Cited

U.S. PATENT DOCUMENTS 8,226,569 B2 * 7/2012 Sotos ..................... A61B 5/742
600/529
9,358,353 B2 6/2016 Armitstead et al.
(Continued)

FOREIGN PATENT DOCUMENTS

CN 1803089 A 7/2006
CN 103690168 A 4/2014
(Continued)

OTHER PUBLICATIONS

Written Opinion in International Patent Application No. PCT/IB2021/055714 mailed Sep. 30, 2021 (6 pp.).
(Continued)

*Primary Examiner* — Timothy A Stanis
*Assistant Examiner* — Matthew D Ziegler
(74) *Attorney, Agent, or Firm* — Nixon Peabody LLP

(57) ABSTRACT

A method includes data associated with a sleep session of a user, including respiration data associated with the user during at least a portion of the sleep session and audio data reproducible as one or more sounds during at least a portion of the sleep session. The method also includes determining a respiration signal associated with the user during the sleep session based, at least in part, on at least a portion of the data. The method also includes identifying an event experienced by the user during the sleep session based, at least in part on, at least a portion of the data. The method also includes causing to be communicated to the user via a user device a graphical representation of a portion of the respiration signal and an event indication that aids in identifying the identified
(Continued)

event within the graphical representation of the portion of the respiration signal.

22 Claims, 8 Drawing Sheets

(58) Field of Classification Search
CPC ........ A61M 16/021; A61M 2205/3375; A61M 2205/505; A61M 2230/42; G06F 3/1645
See application file for complete search history.

(56) References Cited

U.S. PATENT DOCUMENTS

| | | | | |
|---|---|---|---|---|
| 10,328,219 | B2 | 6/2019 | Rao et al. | |
| 2004/0015079 | A1* | 1/2004 | Berger | G01S 7/5208 600/443 |
| 2006/0212273 | A1* | 9/2006 | Krausman | A61B 5/4818 702/189 |
| 2009/0082639 | A1* | 3/2009 | Pittman | A61B 5/0205 600/300 |
| 2014/0088373 | A1 | 3/2014 | Phillips et al. | |
| 2016/0193437 | A1* | 7/2016 | Bao | A61M 16/1075 128/203.14 |
| 2017/0311879 | A1 | 11/2017 | Armitstead et al. | |
| 2018/0256069 | A1* | 9/2018 | Mcmahon | A61B 5/0826 |
| 2020/0086076 | A1* | 3/2020 | Mcelhone | G10K 11/1752 |
| 2020/0383580 | A1 | 12/2020 | Shouldice et al. | |
| 2022/0139544 | A1* | 5/2022 | Lawlor | G16H 50/30 705/2 |

FOREIGN PATENT DOCUMENTS

| | | | |
|---|---|---|---|
| CN | 104257368 | A | 1/2015 |
| CN | 104812300 | A | 7/2015 |
| CN | 105592777 | A | 5/2016 |
| CN | 109937010 | A | 6/2019 |
| CN | 109952058 | A | 6/2019 |
| CN | 110831497 | A | 2/2020 |
| JP | 2014210137 | A | 11/2014 |
| JP | 2015117996 | A | 6/2015 |
| JP | 2016533797 | A | 11/2016 |
| WO | 2008/138040 | A1 | 11/2008 |
| WO | 2012/012835 | A2 | 2/2012 |
| WO | 2014/047310 | A1 | 3/2014 |
| WO | 2015/006364 | A2 | 1/2015 |
| WO | 2016/061629 | A1 | 4/2016 |
| WO | 2017/029317 | A1 | 2/2017 |
| WO | 2017/132726 | A1 | 8/2017 |
| WO | 2018/050913 | A1 | 3/2018 |
| WO | 2019/122413 | A1 | 6/2019 |
| WO | 2019/122414 | A1 | 6/2019 |
| WO | 2020/104465 | A2 | 5/2020 |

OTHER PUBLICATIONS

International Search Report in International Patent Application No. PCT/IB2021/055714 mailed Sep. 30, 2021 (4 pp.).

* cited by examiner

SYSTEMS AND METHODS FOR COMMUNICATING AN INDICATION OF A SLEEP-RELATED EVENT TO A USER

CROSS-REFERENCE TO RELATED APPLICATIONS

This application is a U.S. National Stage of International Application No. PCT/IB2021/055714, filed Jun. 25, 2021, which claims the benefit of, and priority to, U.S. Provisional Patent Application No. 63/044,760, filed on Jun. 26, 2020, both of which is hereby incorporated by reference herein in its entirety.

TECHNICAL FIELD

The present disclosure relates generally to systems and methods for identifying an event experienced by a user during a sleep session, and more particularly, to systems and methods for communicating one or more visual and/or audio indications of an identified event to the user.

BACKGROUND

Many individuals suffer from sleep-related and/or respiratory disorders such as, for example, Periodic Limb Movement Disorder (PLMD), Restless Leg Syndrome (RLS), Sleep-Disordered Breathing (SDB), Obstructive Sleep Apnea (OSA), apneas, Cheyne-Stokes Respiration (CSR), respiratory insufficiency, Obesity Hyperventilation Syndrome (OHS), Chronic Obstructive Pulmonary Disease (COPD), Neuromuscular Disease (NMD), and chest wall disorders. These disorders are often treated using a respiratory therapy system. However, some users find such systems to be uncomfortable, difficult to use, expensive, aesthetically unappealing and/or fail to perceive the benefits associated with using the system. As a result, some users will elect not to begin using the respiratory therapy system or discontinue use of the respiratory therapy system absent a demonstration of the severity of their symptoms when respiratory therapy treatment is not used. The present disclosure is directed to solving these and other problems.

SUMMARY

According to some implementations of the present disclosure, a method includes receiving, from one or more sensors, data associated with a sleep session of a user. The data includes respiration data associated with the user during at least a portion of the sleep session and audio data reproducible as one or more sounds associated with the user during at least a portion of the sleep session. The method also includes determining a respiration signal associated with the user during the sleep session based, at least in part, on at least a portion of the data. The method also includes identifying an event experienced by the user during the sleep session based, at least in part on, at least a portion of the data. The method also includes causing to be communicated to the user, via a user device, a graphical representation of a portion of the respiration signal and an event indication that aids in identifying the identified event within the graphical representation of the portion of the respiration signal.

According to some implementations of the present disclosure, a system includes an electronic interface, a memory, and a control system. The memory stores machine-readable instructions. The control system includes one or more processors configured to execute the machine-readable instructions to receive data associated with a sleep session of a user, the data including respiration data associated with the user during at least a portion of the sleep session and audio data reproducible as one or more sounds associated with the user during at least a portion of the sleep session. The control system is further configured to determine a respiration signal associated with the user during the sleep session based, at least in part, on at least a portion of the data. The control system is further configured to identify an event experienced by the user during the sleep session based, at least in part on, at least a portion of the data. The control system is further configured to cause to be communicated to the user via a user device a graphical representation of a portion of the respiration signal, and an event indication that aids in identifying the identified event within the graphical representation of the portion of the respiration signal.

The above summary is not intended to represent each implementation or every aspect of the present disclosure. Additional features and benefits of the present disclosure are apparent from the detailed description and figures set forth below.

Figure 1:
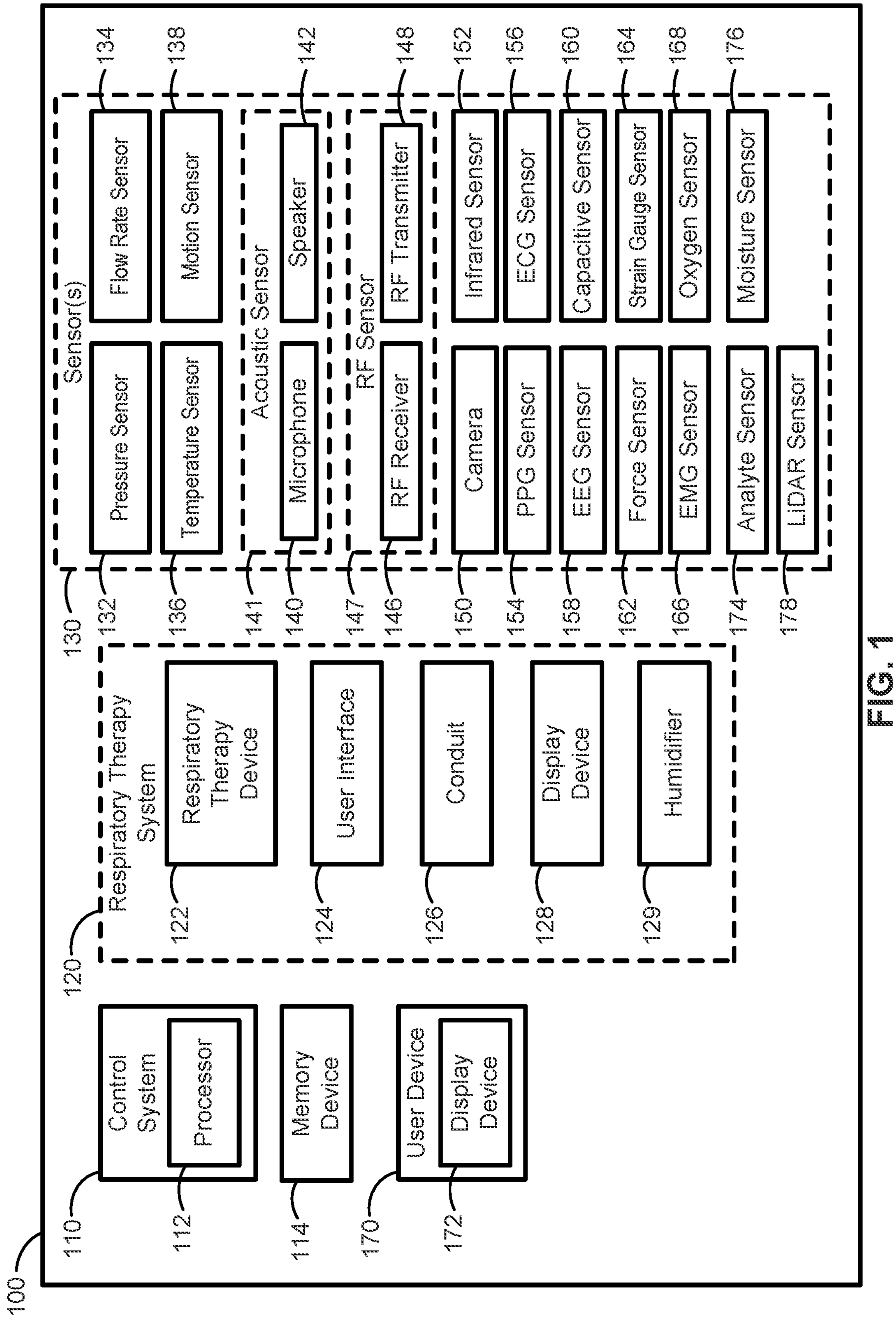
FIG. 1 is a functional block diagram of a system, according to some implementations of the present disclosure.

While the present disclosure is susceptible to various modifications and alternative forms, specific implementations and embodiments thereof have been shown by way of example in the drawings and will herein be described in detail. It should be understood, however, that it is not intended to limit the present disclosure to the particular forms disclosed, but on the contrary, the present disclosure is to cover all modifications, equivalents, and alternatives falling within the spirit and scope of the present disclosure as defined by the appended claims.

DETAILED DESCRIPTION

Many individuals suffer from sleep-related and/or respiratory disorders. Examples of sleep-related and/or respiratory disorders include Periodic Limb Movement Disorder (PLMD), Restless Leg Syndrome (RLS), Sleep-Disordered Breathing (SDB) such as Obstructive Sleep Apnea (OSA), Central Sleep Apnea (CSA), and other types of apneas such as mixed apneas and hypopneas, Respiratory Effort Related Arousal (RERA), Cheyne-Stokes Respiration (CSR), respiratory insufficiency, Obesity Hyperventilation Syndrome (OHS), Chronic Obstructive Pulmonary Disease (COPD), Neuromuscular Disease (NMD), rapid eye movement (REM) behavior disorder (also referred to as RBD), dream enactment behavior (DEB), hypertension, diabetes, stroke, insomnia, and chest wall disorders. These disorders are often treated using a respiratory therapy system.

Obstructive Sleep Apnea (OSA) is a form of Sleep Disordered Breathing (SDB), and is characterized by events including occlusion or obstruction of the upper air passage during sleep resulting from a combination of an abnormally small upper airway and the normal loss of muscle tone in the region of the tongue, soft palate and posterior oropharyngeal wall. More generally, an apnea generally refers to the cessation of breathing caused by blockage of the air (Obstructive Sleep Apnea) or the stopping of the breathing function (often referred to as Central Sleep Apnea). Typically, the individual will stop breathing for between about 15 seconds and about 30 seconds during an obstructive sleep apnea event.

Other types of apneas include hypopnea, hyperpnea, and hypercapnia. Hypopnea is generally characterized by slow or shallow breathing caused by a narrowed airway, as opposed to a blocked airway. Hyperpnea is generally characterized by an increase depth and/or rate of breathin. Hypercapnia is generally characterized by elevated or excessive carbon dioxide in the bloodstream, typically caused by inadequate respiration.

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterized by repetitive de-oxygenation and re-oxygenation of the arterial blood.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common, such as increased resistance to air movement, extended expiratory phase of respiration, and loss of the normal elasticity of the lung.

Neuromuscular Disease (NMD) encompasses many diseases and ailments that impair the functioning of the muscles either directly via intrinsic muscle pathology, or indirectly via nerve pathology. Chest wall disorders are a group of thoracic deformities that result in inefficient coupling between the respiratory muscles and the thoracic cage.

A Respiratory Effort Related Arousal (RERA) event is typically characterized by an increased respiratory effort for ten seconds or longer leading to arousal from sleep and which does not fulfill the criteria for an apnea or hypopnea event. RERAs are defined as a sequence of breaths characterized by increasing respiratory effort leading to an arousal from sleep, but which does not meet criteria for an apnea or hypopnea. These events must fulfil both of the following criteria: (1) a pattern of progressively more negative esophageal pressure, terminated by a sudden change in pressure to a less negative level and an arousal, and (2) the event lasts ten seconds or longer. In some implementations, a Nasal Cannula/Pressure Transducer System is adequate and reliable in the detection of RERAs. A RERA detector may be based on a real flow signal derived from a respiratory therapy device. For example, a flow limitation measure may be determined based on a flow signal. A measure of arousal may then be derived as a function of the flow limitation measure and a measure of sudden increase in ventilation. One such method is described in WO 2008/138040 and U.S. Pat. No. 9,358,353, assigned to ResMed Ltd., the disclosure of each of which is hereby incorporated by reference herein in their entireties.

These and other disorders are characterized by particular events (e.g., snoring, an apnea, a hypopnea, a restless leg, a sleeping disorder, choking, an increased heart rate, labored breathing, an asthma attack, an epileptic episode, a seizure, or any combination thereof) that occur when the individual is sleeping.

The Apnea-Hypopnea Index (AHI) is an index used to indicate the severity of sleep apnea during a sleep session. The AHI is calculated by dividing the number of apnea and/or hypopnea events experienced by the user during the sleep session by the total number of hours of sleep in the sleep session. The event can be, for example, a pause in breathing that lasts for at least 10 seconds. An AHI that is less than 5 is considered normal. An AHI that is greater than or equal to 5, but less than 15 is considered indicative of mild sleep apnea. An AHI that is greater than or equal to 15, but less than 30 is considered indicative of moderate sleep apnea. An AHI that is greater than or equal to 30 is considered indicative of severe sleep apnea. In children, an AHI that is greater than 1 is considered abnormal. Sleep apnea can be considered "controlled" when the AHI is normal, or when the AHI is normal or mild. The AHI can also be used in combination with oxygen desaturation levels to indicate the severity of Obstructive Sleep Apnea.

Referring to FIG. 1, a system 100, according to some implementations of the present disclosure, is illustrated. The system 100 includes a control system 110, a memory device 114, one or more sensors 130, and one or more user devices 170. In some implementations, the system 100 further optionally includes a respiratory therapy system 120.

The control system 110 includes one or more processors 112 (hereinafter, processor 112). The control system 110 is generally used to control (e.g., actuate) the various components of the system 100 and/or analyze data obtained and/or generated by the components of the system 100. The processor 112 can be a general or special purpose processor or microprocessor. While one processor 112 is illustrated in FIG. 1, the control system 110 can include any number of processors (e.g., one processor, two processors, five processors, ten processors, etc.) that can be in a single housing, or located remotely from each other. The control system 110 (or any other control system) or a portion of the control system 110 such as the processor 112 (or any other processor(s) or portion(s) of any other control system), can be used to carry out one or more steps of any of the methods described and/or claimed herein. The control system 110 can be coupled to and/or positioned within, for example, a housing of the user device 170, a portion (e.g., the respiratory therapy device 122) of the respiratory therapy system 120, and/or within a housing of one or more of the sensors 130. The control system 110 can be centralized (within one such housing) or decentralized (within two or more of such housings, which are physically distinct). In such implementations including two or more housings containing the control system 110, such housings can be located proximately and/or remotely from each other.

The memory device 114 stores machine-readable instructions that are executable by the processor 112 of the control system 110. The memory device 114 can be any suitable computer readable storage device or media, such as, for example, a random or serial access memory device, a hard drive, a solid state drive, a flash memory device, etc. While one memory device 114 is shown in FIG. 1, the system 100 can include any suitable number of memory devices 114 (e.g., one memory device, two memory devices, five memory devices, ten memory devices, etc.). The memory device 114 can be coupled to and/or positioned within a housing of the respiratory therapy device 122, within a housing of the user device 170, within a housing of one or more of the sensors 130, or any combination thereof. Like the control system 110, the memory device 114 can be centralized (within one such housing) or decentralized (within two or more of such housings, which are physically distinct).

In some implementations, the memory device 114 (FIG. 1) stores a user profile associated with the user. The user profile can include, for example, demographic information associated with the user, biometric information associated with the user, medical information associated with the user, self-reported user feedback, sleep parameters associated with the user (e.g., sleep-related parameters recorded from one or more earlier sleep sessions), or any combination thereof. The demographic information can include, for example, information indicative of an age of the user, a gender of the user, a race of the user, a family history of insomnia, an employment status of the user, an educational status of the user, a socioeconomic status of the user, or any combination thereof. The medical information can include, for example, including indicative of one or more medical conditions associated with the user, medication usage by the user, or both. The medical information data can further include a multiple sleep latency test (MSLT) test result or score and/or a Pittsburgh Sleep Quality Index (PSQI) score or value. The self-reported user feedback can include information indicative of a self-reported subjective sleep score (e.g., poor, average, excellent), a self-reported subjective stress level of the user, a self-reported subjective fatigue level of the user, a self-reported subjective health status of the user, a recent life event experienced by the user, or any combination thereof.

As described herein, the processor 112 of the control system 110 and/or memory device 114 can receive data (e.g., physiological data and/or audio data) from the one or more sensors 130 such that the data for storage in the memory device 114 and/or for analysis by the processor 112. The processor 112 and/or memory device 114 can communicate with the one or more sensors 130 using a wired connection or a wireless connection (e.g., using an RF communication protocol, a Wi-Fi communication protocol, a Bluetooth communication protocol, over a cellular network, etc.). In some implementations, the system 100 can include an antenna, a receiver (e.g., an RF receiver), a transmitter (e.g., an RF transmitter), a transceiver, or any combination thereof. Such components can be coupled to or integrated a housing of the control system 110 (e.g., in the same housing as the processor 112 and/or memory device 114), or the user device 170.

As noted above, in some implementations, the system 100 optionally includes a respiratory therapy system 120. The respiratory therapy system 120 includes a respiratory pressure therapy device 122 (referred to herein as respiratory therapy device 122), a user interface 124 (also referred to as a mask or patient interface), a conduit 126 (also referred to as a tube or an air circuit), a display device 128, a humidifier 129, or any combination thereof. In some implementations, the control system 110, the memory device 114, the display device 128, one or more of the sensors 130, and the humidifier 129 are part of the respiratory therapy device 122. Respiratory pressure therapy refers to the application of a supply of air to an entrance to a user's airways at a controlled target pressure that is nominally positive with respect to atmosphere throughout the user's breathing cycle (e.g., in contrast to negative pressure therapies such as the tank ventilator or cuirass). The respiratory therapy system 120 is generally used to treat individuals suffering from one or more sleep-related respiratory disorders (e.g., obstructive sleep apnea, central sleep apnea, or mixed sleep apnea).

The respiratory therapy device 122 is generally used to generate pressurized air that is delivered to a user (e.g., using one or more motors that drive one or more compressors). In some implementations, the respiratory therapy device 122 generates continuous constant air pressure that is delivered to the user. In other implementations, the respiratory therapy device 122 generates two or more predetermined pressures (e.g., a first predetermined air pressure and a second predetermined air pressure). In still other implementations, the respiratory therapy device 122 is configured to generate a variety of different air pressures within a predetermined range. For example, the respiratory therapy device 122 can deliver at least about 6 cm $H_2O$, at least about 10 cm $H_2O$, at least about 20 cm $H_2O$, between about 6 cm $H_2O$ and about 10 cm $H_2O$, between about 7 cm $H_2O$ and about 12 cm $H_2O$, etc. The respiratory therapy device 122 can also deliver pressurized air at a predetermined flow rate between, for example, about −20 L/min and about 150 L/min, while maintaining a positive pressure (relative to the ambient pressure).

The user interface 124 engages a portion of the user's face and delivers pressurized air from the respiratory therapy device 122 to the user's airway to aid in preventing the airway from narrowing and/or collapsing during sleep. This may also increase the user's oxygen intake during sleep. Generally, the user interface 124 engages the user's face such that the pressurized air is delivered to the user's airway via the user's mouth, the user's nose, or both the user's mouth and nose. Together, the respiratory therapy device 122, the user interface 124, and the conduit 126 form an air pathway fluidly coupled with an airway of the user. The pressurized air also increases the user's oxygen intake during sleep. Depending upon the therapy to be applied, the user interface 124 may form a seal, for example, with a region or portion of the user's face, to facilitate the delivery of gas at a pressure at sufficient variance with ambient pressure to effect therapy, for example, at a positive pressure of about 10 cm $H_2O$ relative to ambient pressure. For other forms of therapy, such as the delivery of oxygen, the user interface may not include a seal sufficient to facilitate delivery to the airways of a supply of gas at a positive pressure of about 10 cm $H_2O$.

Figure 2:
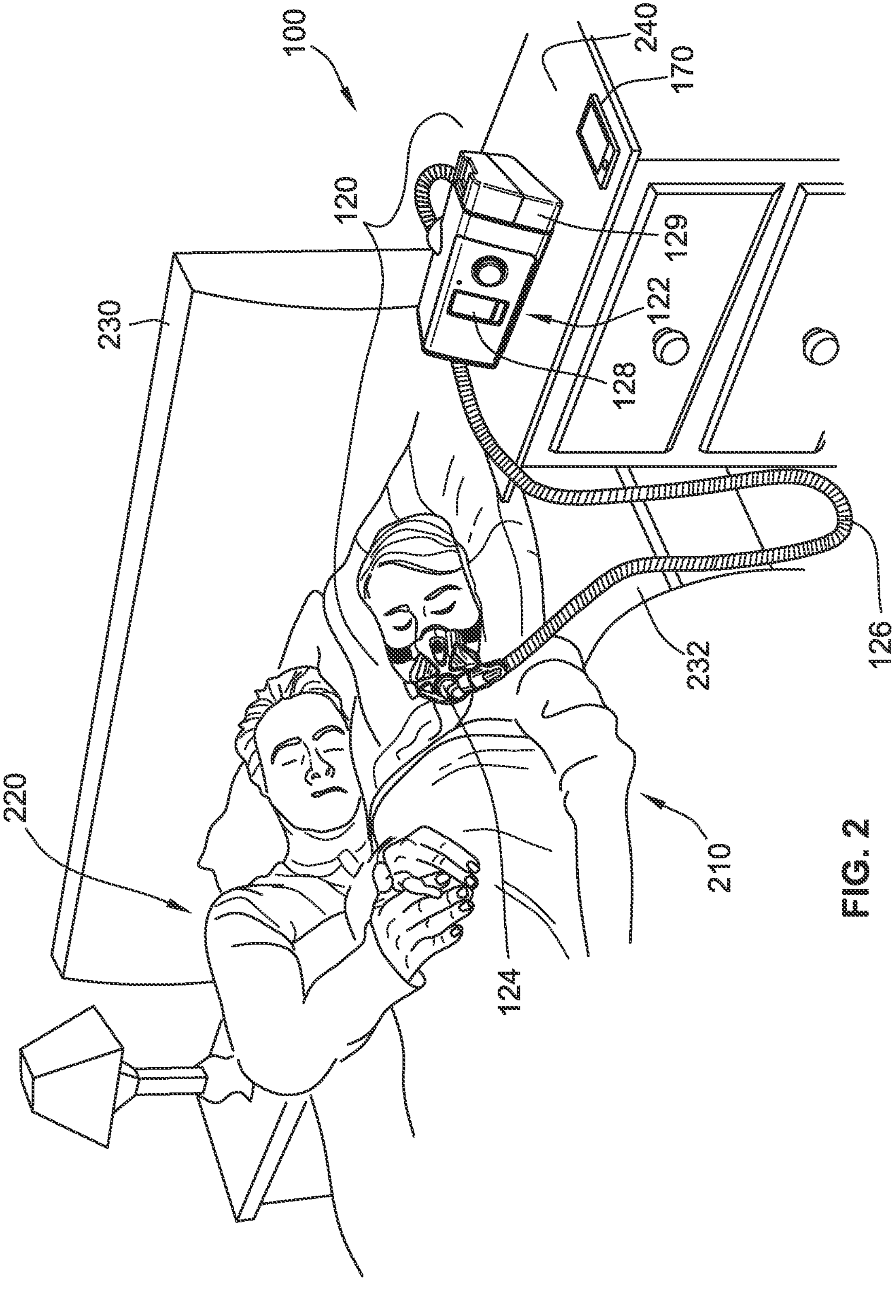
FIG. 2 is a perspective view of at least a portion of the system of FIG. 1, a user, and a bed partner, according to some implementations of the present disclosure.

As shown in FIG. 2, in some implementations, the user interface 124 is a facial mask that covers the nose and mouth of the user. Alternatively, the user interface 124 can be a nasal mask that provides air to the nose of the user or a nasal pillow mask that delivers air directly to the nostrils of the user. The user interface 124 can include a plurality of straps (e.g., including hook and loop fasteners) for positioning and/or stabilizing the interface on a portion of the user (e.g., the face) and a conformal cushion (e.g., silicone, plastic, foam, etc.) that aids in providing an air-tight seal between the user interface 124 and the user. The user interface 124 can also include one or more vents for permitting the escape of carbon dioxide and other gases exhaled by the user 210.

In other implementations, the user interface 124 is a mouthpiece (e.g., a night guard mouthpiece molded to conform to the user's teeth, a mandibular repositioning device, etc.) for directing pressurized air into the mouth of the user.

The conduit 126 (also referred to as an air circuit or tube) allows the flow of air between two components of a respiratory therapy system 120, such as the respiratory therapy device 122 and the user interface 124. In some implementations, there can be separate limbs of the conduit for inhalation and exhalation. In other implementations, a single limb conduit is used for both inhalation and exhalation. The conduit 126 includes a first end coupled to an outlet of the respiratory therapy device 122 and a second opposing end coupled to the user interface 124. The conduit 126 can be coupled to the respiratory therapy device 122 and/or the user interface 124 using a variety of techniques (e.g., a press fit connection, a snap fit connection, a threaded connection, etc.). In some implementations, the conduit 126 includes one or more heating elements that heat the pressurized air flowing through the conduit 126 (e.g., heat the air to a predetermined temperature or within a range of predetermined temperatures). Such heating elements can be coupled to and/or imbedded in the conduit 126. In such implementations, the end of the conduit 126 coupled to the respiratory therapy device 122 can include an electrical contact that is electrically coupled to the respiratory therapy device 122 to power the one or more heating elements of the conduit 126.

One or more of the respiratory therapy device 122, the user interface 124, the conduit 126, the display device 128, and the humidifier 129 can contain one or more sensors (e.g., a pressure sensor, a flow rate sensor, or more generally any of the other sensors 130 described herein). These one or more sensors can be use, for example, to measure the air pressure and/or flow rate of pressurized air supplied by the respiratory therapy device 122.

The display device 128 is generally used to display image(s) including still images, video images, or both and/or information regarding the respiratory therapy device 122. For example, the display device 128 can provide information regarding the status of the respiratory therapy device 122 (e.g., whether the respiratory therapy device 122 is on/off, the pressure of the air being delivered by the respiratory therapy device 122, the temperature of the air being delivered by the respiratory therapy device 122, etc.) and/or other information ((e.g., a sleep score and/or a therapy score, also referred to as a myAir™ score, such as described in WO 2016/061629 and U.S. Patent Pub. No. 2017/0311879, which are hereby incorporated by reference herein in their entireties, the current date/time, personal information for the user, etc.). In some implementations, the display device 128 acts as a human-machine interface (HMI) that includes a graphic user interface (GUI) configured to display the image(s) as an input interface. The display device 128 can be an LED display, an OLED display, an LCD display, or the like. The input interface can be, for example, a touchscreen or touch-sensitive substrate, a mouse, a keyboard, or any sensor system configured to sense inputs made by a human user interacting with the respiratory therapy device 122.

The humidifier 129 is coupled to or integrated in the respiratory therapy device 122 and includes a reservoir of water that can be used to humidify the pressurized air delivered from the respiratory therapy device 122. The respiratory therapy device 122 can include a heater to heat the water in the humidifier 129 in order to humidify the pressurized air provided to the user. Additionally, in some implementations, the conduit 126 can also include a heating element (e.g., coupled to and/or imbedded in the conduit 126) that heats the pressurized air delivered to the user.

The respiratory therapy system 120 can be used, for example, as a ventilator or as a positive airway pressure (PAP) system, such as a continuous positive airway pressure (CPAP) system, an automatic positive airway pressure system (APAP), a bi-level or variable positive airway pressure system (BPAP or VPAP), or any combination thereof. The CPAP system delivers a predetermined air pressure (e.g., determined by a sleep physician) to the user. The APAP system automatically varies the air pressure delivered to the user based on, for example, respiration data associated with the user. The BPAP or VPAP system is configured to deliver a first predetermined pressure (e.g., an inspiratory positive airway pressure or IPAP) and a second predetermined pressure (e.g., an expiratory positive airway pressure or EPAP) that is lower than the first predetermined pressure).

Referring to FIG. 2, a portion of the system 100 (FIG. 1), according to some implementations, is illustrated. A user 210 of the respiratory therapy system 120 and a bed partner 220 are located in a bed 230 and are laying on a mattress 232. The user interface 124 (e.g., a full facial mask) can be worn by the user 210 during a sleep session. The user interface 124 is fluidly coupled and/or connected to the respiratory therapy device 122 via the conduit 126. In turn, the respiratory therapy device 122 delivers pressurized air to the user 210 via the conduit 126 and the user interface 124 to increase the air pressure in the throat of the user 210 to aid in preventing the airway from closing and/or narrowing during sleep. The respiratory therapy device 122 can be positioned on a nightstand 240 that is directly adjacent to the bed 230 as shown in FIG. 2, or more generally, on any surface or structure that is generally adjacent to the bed 230 and/or the user 210.

Referring to back to FIG. 1, the one or more sensors 130 of the system 100 include a pressure sensor 132, a flow rate sensor 134, temperature sensor 136, a motion sensor 138, a microphone 140, a speaker 142, a radio-frequency (RF) receiver 146, a RF transmitter 148, a camera 150, an infrared sensor 152, a photoplethysmogram (PPG) sensor 154, an electrocardiogram (ECG) sensor 156, an electroencephalography (EEG) sensor 158, a capacitive sensor 160, a force sensor 162, a strain gauge sensor 164, an electromyography (EMG) sensor 166, an oxygen sensor 168, an analyte sensor 174, a moisture sensor 176, a LiDAR sensor 178, or any combination thereof. Generally, each of the one or sensors 130 are configured to output sensor data that is received and stored in the memory device 114 or one or more other memory devices.

While the one or more sensors 130 are shown and described as including each of the pressure sensor 132, the flow rate sensor 134, the temperature sensor 136, the motion sensor 138, the microphone 140, the speaker 142, the RF receiver 146, the RF transmitter 148, the camera 150, the infrared sensor 152, the photoplethysmogram (PPG) sensor 154, the electrocardiogram (ECG) sensor 156, the electroencephalography (EEG) sensor 158, the capacitive sensor 160, the force sensor 162, the strain gauge sensor 164, the electromyography (EMG) sensor 166, the oxygen sensor 168, the analyte sensor 174, the moisture sensor 176, and the LiDAR sensor 178, more generally, the one or more sensors 130 can include any combination and any number of each of the sensors described and/or shown herein.

The one or more sensors 130 can be used to generate, for example, physiological data, audio data, or both. Physiological data generated by one or more of the sensors 130 can be used by the control system 110 to determine a sleep-wake signal associated with a user during a sleep session and one or more sleep-related parameters. The sleep-wake signal can be indicative of one or more sleep states, including wakefulness, relaxed wakefulness, micro-awakenings, a rapid eye movement (REM) stage, a first non-REM stage (often referred to as "N1"), a second non-REM stage (often referred to as "N2"), a third non-REM stage (often referred to as "N3"), or any combination thereof. Methods for determining sleep states and/or sleep stages from physiological data generated by one or more sensors, such as the one or more sensors 210, are described in, for example, WO 2014/047310, U.S. Patent Pub. No. 2014/0088373, WO 2017/132726, WO 2019/122413, WO 2019/122414, and U.S. Patent Pub. No. 2020/0383580 each of which is hereby incorporated by reference herein in its entirety. The sleep-wake signal can be measured by the sensor(s) 130 during the sleep session at a predetermined sampling rate, such as, for example, one sample per second, one sample per 30 seconds, one sample per minute, etc. Examples of the one or more sleep-related parameters that can be determined for the user during the sleep session based on the sleep-wake signal include a total time in bed, a total sleep time, a sleep onset latency, a wake-after-sleep-onset parameter, a sleep efficiency, a fragmentation index, or any combination thereof.

The sleep-wake signal can also be timestamped to indicate a time that the user enters the bed, a time that the user exits the bed, a time that the user attempts to fall asleep, etc. The sleep-wake signal can be measured by the one or more sensors 130 during the sleep session at a predetermined sampling rate, such as, for example, one sample per second, one sample per 30 seconds, one sample per minute, etc. In some implementations, the sleep-wake signal can also be indicative of a respiration signal, a respiration rate, an inspiration amplitude, an expiration amplitude, an inspiration-expiration ratio, a number of events per hour, a pattern of events, pressure settings of the respiratory therapy device 122, or any combination thereof during the sleep session. The event(s) can include snoring, apneas, central apneas, obstructive apneas, mixed apneas, hypopneas, a mask leak (e.g., from the user interface 124), a restless leg, a sleeping disorder, choking, an increased heart rate, labored breathing, an asthma attack, an epileptic episode, a seizure, or any combination thereof. The one or more sleep-related parameters that can be determined for the user during the sleep session based on the sleep-wake signal include, for example, a total time in bed, a total sleep time, a sleep onset latency, a wake-after-sleep-onset parameter, a sleep efficiency, a fragmentation index, or any combination thereof. As described in further detail herein, the physiological data and/or the sleep-related parameters can be analyzed to determine one or more sleep-related scores.

Physiological data and/or audio data generated by the one or more sensors 130 can also be used to determine a respiration signal associated with a user during a sleep session. The respiration signal is generally indicative of respiration or breathing of the user during the sleep session. The respiration signal can be indicative of, for example, a respiration rate, a respiration rate variability, an inspiration amplitude, an expiration amplitude, an inspiration-expiration ratio, a number of events per hour, a pattern of events, pressure settings of the respiratory therapy device 122, or any combination thereof. The event(s) can include snoring, apneas, central apneas, obstructive apneas, mixed apneas, hypopneas, a mask leak (e.g., from the user interface 124), a restless leg, a sleeping disorder, choking, an increased heart rate, labored breathing, an asthma attack, an epileptic episode, a seizure, or any combination thereof.

The pressure sensor 132 outputs pressure data that can be stored in the memory device 114 and/or analyzed by the processor 112 of the control system 110. In some implementations, the pressure sensor 132 is an air pressure sensor (e.g., barometric pressure sensor) that generates sensor data indicative of the respiration (e.g., inhaling and/or exhaling) of the user of the respiratory therapy system 120 and/or ambient pressure. In such implementations, the pressure sensor 132 can be coupled to or integrated in the respiratory therapy device 122. The pressure sensor 132 can be, for example, a capacitive sensor, an electromagnetic sensor, a piezoelectric sensor, a strain-gauge sensor, an optical sensor, a potentiometric sensor, or any combination thereof.

The flow rate sensor 134 outputs flow rate data that can be stored in the memory device 114 and/or analyzed by the processor 112 of the control system 110. Examples of flow rate sensors (such as, for example, the flow rate sensor 134) are described in International Publication No. WO 2012/012835 and U.S. Pat. No. 10,328,219, both of which are hereby incorporated by reference herein in their entireties. In some implementations, the flow rate sensor 134 is used to determine an air flow rate from the respiratory therapy device 122, an air flow rate through the conduit 126, an air flow rate through the user interface 124, or any combination thereof. In such implementations, the flow rate sensor 134 can be coupled to or integrated in the respiratory therapy device 122, the user interface 124, or the conduit 126. The flow rate sensor 134 can be a mass flow rate sensor such as, for example, a rotary flow meter (e.g., Hall effect flow meters), a turbine flow meter, an orifice flow meter, an ultrasonic flow meter, a hot wire sensor, a vortex sensor, a membrane sensor, or any combination thereof.

The temperature sensor 136 outputs temperature data that can be stored in the memory device 114 and/or analyzed by the processor 112 of the control system 110. In some implementations, the temperature sensor 136 generates temperatures data indicative of a core body temperature of the user 210 (FIG. 2), a skin temperature of the user 210, a temperature of the air flowing from the respiratory therapy device 122 and/or through the conduit 126, a temperature in the user interface 124, an ambient temperature, or any combination thereof. The temperature sensor 136 can be, for example, a thermocouple sensor, a thermistor sensor, a silicon band gap temperature sensor or semiconductor-based sensor, a resistance temperature detector, or any combination thereof.

The motion sensor 138 outputs motion data that can be stored in the memory device 114 and/or analyzed by the processor 112 of the control system 110. The motion sensor 138 can be used to detect movement of the user 210 during the sleep session, and/or detect movement of any of the components of the respiratory therapy system 120, such as the respiratory therapy device 122, the user interface 124, or the conduit 126. The motion sensor 138 can include one or more inertial sensors, such as accelerometers, gyroscopes, and magnetometers. In some implementations, the motion sensor 138 alternatively or additionally generates one or more signals representing bodily movement of the user, from which may be obtained a signal representing a sleep state of the user; for example, via a respiratory movement of the user. In some implementations, the motion data from the motion sensor 138 can be used in conjunction with additional data from another one of the sensors 130 to determine the sleep state of the user.

The microphone 140 outputs audio data that can be stored in the memory device 114 and/or analyzed by the processor 112 of the control system 110. The audio data generated by the microphone 140 is reproducible as one or more sound(s) during a sleep session (e.g., sounds from the user 210). The audio data form the microphone 140 can also be used to identify (e.g., using the control system 110) an event experienced by the user during the sleep session, as described in further detail herein. The microphone 140 can be coupled to or integrated in the respiratory therapy device 122, the user interface 124, the conduit 126, or the user device 170. In some implementations, the system 100 includes a plurality of microphones (e.g., two or more microphones and/or an array of microphones with beamforming) such that sound data generated by each of the plurality of microphones can be used to discriminate the sound data generated by another of the plurality of microphones.

The speaker 142 outputs sound waves that are audible to a user of the system 100 (e.g., the user 210 of FIG. 2). The speaker 142 can be used, for example, as an alarm clock or to play an alert or message to the user 210 (e.g., in response to an event). In some implementations, the speaker 142 can be used to communicate the audio data generated by the microphone 140 to the user. The speaker 142 can be coupled to or integrated in the respiratory therapy device 122, the user interface 124, the conduit 126, or the user device 170.

The microphone 140 and the speaker 142 can be used as separate devices. In some implementations, the microphone 140 and the speaker 142 can be combined into an acoustic sensor 141 (e.g., a SONAR sensor), as described in, for example, WO 2018/050913 and WO 2020/104465, which is hereby incorporated by reference herein in its entirety. In such implementations, the speaker 142 generates or emits sound waves at a predetermined interval and the microphone 140 detects the reflections of the emitted sound waves from the speaker 142. The sound waves generated or emitted by the speaker 142 have a frequency that is not audible to the human ear (e.g., below 20 Hz or above around 18 kHz) so as not to disturb the sleep of the user 210 or the bed partner 220 (FIG. 2). Based at least in part on the data from the microphone 140 and/or the speaker 142, the control system 110 can determine a location of the user 210 (FIG. 2) and/or one or more of the sleep-related parameters described in herein.

In some implementations, the sensors 130 include (i) a first microphone that is the same as, or similar to, the microphone 140, and is integrated in the acoustic sensor 141 and (ii) a second microphone that is the same as, or similar to, the microphone 140, but is separate and distinct from the first microphone that is integrated in the acoustic sensor 141.

The RF transmitter 148 generates and/or emits radio waves having a predetermined frequency and/or a predetermined amplitude (e.g., within a high frequency band, within a low frequency band, long wave signals, short wave signals, etc.). The RF receiver 146 detects the reflections of the radio waves emitted from the RF transmitter 148, and this data can be analyzed by the control system 110 to determine a location of the user 210 (FIG. 2) and/or one or more of the sleep-related parameters described herein. An RF receiver (either the RF receiver 146 and the RF transmitter 148 or another RF pair) can also be used for wireless communication between the control system 110, the respiratory therapy device 122, the one or more sensors 130, the user device 170, or any combination thereof. While the RF receiver 146 and RF transmitter 148 are shown as being separate and distinct elements in FIG. 1, in some implementations, the RF receiver 146 and RF transmitter 148 are combined as a part of an RF sensor 147. In some such implementations, the RF sensor 147 includes a control circuit. The specific format of the RF communication can be Wi-Fi, Bluetooth, or the like.

In some implementations, the RF sensor 147 is a part of a mesh system. One example of a mesh system is a Wi-Fi mesh system, which can include mesh nodes, mesh router(s), and mesh gateway(s), each of which can be mobile/movable or fixed. In such implementations, the Wi-Fi mesh system includes a Wi-Fi router and/or a Wi-Fi controller and one or more satellites (e.g., access points), each of which include an RF sensor that the is the same as, or similar to, the RF sensor 147. The Wi-Fi router and satellites continuously communicate with one another using Wi-Fi signals. The Wi-Fi mesh system can be used to generate motion data based on changes in the Wi-Fi signals (e.g., differences in received signal strength) between the router and the satellite(s) due to an object or person moving partially obstructing the signals. The motion data can be indicative of motion, breathing, heart rate, gait, falls, behavior, etc., or any combination thereof.

The camera 150 outputs image data reproducible as one or more images (e.g., still images, video images, thermal images, or a combination thereof) that can be stored in the memory device 114. The image data from the camera 150 can be used by the control system 110 to determine one or more of the sleep-related parameters described herein, such as, for example, one or more events (e.g., periodic limb movement or restless leg syndrome), a respiration signal, a respiration rate, an inspiration amplitude, an expiration amplitude, an inspiration-expiration ratio, a number of events per hour, a pattern of events, a sleep state, a sleep stage, or any combination thereof. Further, the image data from the camera 150 can be used to, for example, identify a location of the user, to determine chest movement of the user 210 (FIG. 2), to determine air flow of the mouth and/or nose of the user 210, to determine a time when the user 210 enters the bed 230 (FIG. 2), and to determine a time when the user 210 exits the bed 230. In some implementations, the camera 150 includes a wide angle lens or a fish eye lens. For example, the image data from the camera 150 can be used to identify a location of the user, to determine a time when the user 210 enters the bed 230 (FIG. 2), and to determine a time when the user 210 exits the bed 230.

The infrared (IR) sensor 152 outputs infrared image data reproducible as one or more infrared images (e.g., still images, video images, or both) that can be stored in the memory device 114. The infrared data from the IR sensor 152 can be used to determine one or more sleep-related parameters during a sleep session, including a temperature of the user 210 and/or movement of the user 210. The IR sensor 152 can also be used in conjunction with the camera 150 when measuring the presence, location, and/or movement of the user 210. The IR sensor 152 can detect infrared light having a wavelength between about 700 nm and about 1 mm, for example, while the camera 150 can detect visible light having a wavelength between about 380 nm and about 740 nm.

The PPG sensor 154 outputs physiological data associated with the user 210 (FIG. 2) that can be used to determine one or more sleep-related parameters, such as, for example, a heart rate, a heart rate variability, a cardiac cycle, respiration rate, an inspiration amplitude, an expiration amplitude, an inspiration-expiration ratio, estimated blood pressure parameter(s), or any combination thereof. The PPG sensor 154 can be worn by the user 210, embedded in clothing and/or fabric that is worn by the user 210, embedded in and/or coupled to the user interface 124 and/or its associated headgear (e.g., straps, etc.), etc.

The ECG sensor 156 outputs physiological data associated with electrical activity of the heart of the user 210. In some implementations, the ECG sensor 156 includes one or more electrodes that are positioned on or around a portion of the user 210 during the sleep session. The physiological data from the ECG sensor 156 can be used, for example, to determine one or more of the sleep-related parameters described herein.

The EEG sensor 158 outputs physiological data associated with electrical activity of the brain of the user 210. In some implementations, the EEG sensor 158 includes one or more electrodes that are positioned on or around the scalp of the user 210 during the sleep session. The physiological data from the EEG sensor 158 can be used, for example, to determine a sleep state of the user 210 at any given time during the sleep session. In some implementations, the EEG sensor 158 can be integrated in the user interface 124 and/or the associated headgear (e.g., straps, etc.).

The capacitive sensor 160, the force sensor 162, and the strain gauge sensor 164 output data that can be stored in the memory device 114 and used by the control system 110 to determine one or more of the sleep-related parameters described herein. The EMG sensor 166 outputs physiological data associated with electrical activity produced by one or more muscles. The oxygen sensor 168 outputs oxygen data indicative of an oxygen concentration of gas (e.g., in the conduit 126 or at the user interface 124). The oxygen sensor 168 can be, for example, an ultrasonic oxygen sensor, an electrical oxygen sensor, a chemical oxygen sensor, an optical oxygen sensor, or any combination thereof. In some implementations, the one or more sensors 130 also include a galvanic skin response (GSR) sensor, a blood flow sensor, a respiration sensor, a pulse sensor, a sphygmomanometer sensor, an oximetry sensor, or any combination thereof.

The analyte sensor 174 can be used to detect the presence of an analyte in the exhaled breath of the user 210. The data output by the analyte sensor 174 can be stored in the memory device 114 and used by the control system 110 to determine the identity and concentration of any analytes in the breath of the user 210. In some implementations, the analyte sensor 174 is positioned near a mouth of the user 210 to detect analytes in breath exhaled from the user 210's mouth. For example, when the user interface 124 is a facial mask that covers the nose and mouth of the user 210, the analyte sensor 174 can be positioned within the facial mask to monitor the user 210's mouth breathing. In other implementations, such as when the user interface 124 is a nasal mask or a nasal pillow mask, the analyte sensor 174 can be positioned near the nose of the user 210 to detect analytes in breath exhaled through the user's nose. In still other implementations, the analyte sensor 174 can be positioned near the user 210's mouth when the user interface 124 is a nasal mask or a nasal pillow mask. In this implementation, the analyte sensor 174 can be used to detect whether any air is inadvertently leaking from the user 210's mouth. In some implementations, the analyte sensor 174 is a volatile organic compound (VOC) sensor that can be used to detect carbon-based chemicals or compounds. In some implementations, the analyte sensor 174 can also be used to detect whether the user 210 is breathing through their nose or mouth. For example, if the data output by an analyte sensor 174 positioned near the mouth of the user 210 or within the facial mask (in implementations where the user interface 124 is a facial mask) detects the presence of an analyte, the control system 110 can use this data as an indication that the user 210 is breathing through their mouth.

The moisture sensor 176 outputs data that can be stored in the memory device 114 and used by the control system 110. The moisture sensor 176 can be used to detect moisture in various areas surrounding the user (e.g., inside the conduit 126 or the user interface 124, near the user 210's face, near the connection between the conduit 126 and the user interface 124, near the connection between the conduit 126 and the respiratory therapy device 122, etc.). Thus, in some implementations, the moisture sensor 176 can be coupled to or integrated in the user interface 124 or in the conduit 126 to monitor the humidity of the pressurized air from the respiratory therapy device 122. In other implementations, the moisture sensor 176 is placed near any area where moisture levels need to be monitored. The moisture sensor 176 can also be used to monitor the humidity of the ambient environment surrounding the user 210, for example, the air inside the bedroom.

The Light Detection and Ranging (LiDAR) sensor 178 can be used for depth sensing. This type of optical sensor (e.g., laser sensor) can be used to detect objects and build three dimensional (3D) maps of the surroundings, such as of a living space. LiDAR can generally utilize a pulsed laser to make time of flight measurements. LiDAR is also referred to as 3D laser scanning. In an example of use of such a sensor, a fixed or mobile device (such as a smartphone) having a LiDAR sensor 166 can measure and map an area extending 5 meters or more away from the sensor. The LiDAR data can be fused with point cloud data estimated by an electromagnetic RADAR sensor, for example. The LiDAR sensor(s) 178 can also use artificial intelligence (AI) to automatically geofence RADAR systems by detecting and classifying features in a space that might cause issues for RADAR systems, such a glass windows (which can be highly reflective to RADAR). LiDAR can also be used to provide an estimate of the height of a person, as well as changes in height when the person sits down, or falls down, for example. LiDAR may be used to form a 3D mesh representation of an environment. In a further use, for solid surfaces through which radio waves pass (e.g., radio-translucent materials), the LiDAR may reflect off such surfaces, thus allowing a classification of different type of obstacles.

In some implementations, the one or more sensors 130 also include a galvanic skin response (GSR) sensor, a blood flow sensor, a respiration sensor, a pulse sensor, a sphygmomanometer sensor, an oximetry sensor, a sonar sensor, a RADAR sensor, a blood glucose sensor, a color sensor, a pH sensor, an air quality sensor, a tilt sensor, a rain sensor, a soil moisture sensor, a water flow sensor, an alcohol sensor, or any combination thereof.

While shown separately in FIG. 1, any combination of the one or more sensors 130 can be integrated in and/or coupled to any one or more of the components of the system 100, including the respiratory therapy device 122, the user interface 124, the conduit 126, the humidifier 129, the control system 110, the user device 170, or any combination thereof. For example, the microphone 140 and speaker 142 is integrated in and/or coupled to the user device 170 and the pressure sensor 132 and/or flow rate sensor 134 are integrated in and/or coupled to the respiratory therapy device 122. In some implementations, at least one of the one or more sensors 130 is not coupled to the respiratory therapy device 122, the control system 110, or the user device 170, and is positioned generally adjacent to the user 210 during the sleep session (e.g., positioned on or in contact with a portion of the user 210, worn by the user 210, coupled to or positioned on the nightstand, coupled to the mattress, coupled to the ceiling, etc.).

The data from the one or more sensors 130 can be analyzed to determine one or more sleep-related parameters, which can include a respiration signal, a respiration rate, a respiration pattern, an inspiration amplitude, an expiration amplitude, an inspiration-expiration ratio, an occurrence of one or more events, a number of events per hour, a pattern of events, a sleep state, an apnea-hypopnea index (AHI), or any combination thereof. The one or more events can include snoring, apneas, central apneas, obstructive apneas, mixed apneas, hypopneas, a mask leak, a cough, a restless leg, a sleeping disorder, choking, an increased heart rate, labored breathing, an asthma attack, an epileptic episode, a seizure, increased blood pressure, or any combination thereof. Many of these sleep-related parameters are physiological parameters, although some of the sleep-related parameters can be considered to be non-physiological parameters. Other types of physiological and non-physiological parameters can also be determined, either from the data from the one or more sensors 130, or from other types of data.

The user device 170 (FIG. 1) includes a display device 172. The user device 170 can be, for example, a mobile device such as a smart phone, a tablet, a gaming console, a smart watch, a laptop, or the like. Alternatively, the user device 170 can be an external sensing system, a television (e.g., a smart television) or another smart home device (e.g., a smart speaker(s) such as Google Home, Amazon Echo, Alexa etc.). In some implementations, the user device is a wearable device (e.g., a smart watch). The display device 172 is generally used to display image(s) including still images, video images, or both. In some implementations, the display device 172 acts as a human-machine interface (HMI) that includes a graphic user interface (GUI) configured to display the image(s) and an input interface. The display device 172 can be an LED display, an OLED display, an LCD display, or the like. The input interface can be, for example, a touchscreen or touch-sensitive substrate, a mouse, a keyboard, or any sensor system configured to sense inputs made by a human user interacting with the user device 170. In some implementations, one or more user devices can be used by and/or included in the system 100.

While the control system 110 and the memory device 114 are described and shown in FIG. 1 as being a separate and distinct component of the system 100, in some implementations, the control system 110 and/or the memory device 114 are integrated in the user device 170 and/or the respiratory therapy device 122. Alternatively, in some implementations, the control system 110 or a portion thereof (e.g., the processor 112) can be located in a cloud (e.g., integrated in a server, integrated in an Internet of Things (IoT) device, connected to the cloud, be subject to edge cloud processing, etc.), located in one or more servers (e.g., remote servers, local servers, etc., or any combination thereof.

While system 100 is shown as including all of the components described above, more or fewer components can be included in a system for generating physiological data and determining a recommended notification or action for the user according to implementations of the present disclosure. For example, a first alternative system includes the control system 110, the memory device 114, and at least one of the one or more sensors 130. As another example, a second alternative system includes the control system 110, the memory device 114, at least one of the one or more sensors 130, and the user device 170. As yet another example, a third alternative system includes the control system 110, the memory device 114, the respiratory therapy system 120, at least one of the one or more sensors 130, and the user device 170. Thus, various systems can be formed using any portion or portions of the components shown and described herein and/or in combination with one or more other components.

As used herein, a sleep session can be defined in a number of ways based on, for example, an initial start time and an end time. In some implementations, a sleep session is a duration where the user is asleep, that is, the sleep session has a start time and an end time, and during the sleep session, the user does not wake until the end time. That is, any period of the user being awake is not included in a sleep session. From this first definition of sleep session, if the user wakes ups and falls asleep multiple times in the same night, each of the sleep intervals separated by an awake interval is a sleep session.

Alternatively, in some implementations, a sleep session has a start time and an end time, and during the sleep session, the user can wake up, without the sleep session ending, so long as a continuous duration that the user is awake is below an awake duration threshold. The awake duration threshold can be defined as a percentage of a sleep session. The awake duration threshold can be, for example, about twenty percent of the sleep session, about fifteen percent of the sleep session duration, about ten percent of the sleep session duration, about five percent of the sleep session duration, about two percent of the sleep session duration, etc., or any other threshold percentage. In some implementations, the awake duration threshold is defined as a fixed amount of time, such as, for example, about one hour, about thirty minutes, about fifteen minutes, about ten minutes, about five minutes, about two minutes, etc., or any other amount of time.

In some implementations, a sleep session is defined as the entire time between the time in the evening at which the user first entered the bed, and the time the next morning when user last left the bed. Put another way, a sleep session can be defined as a period of time that begins on a first date (e.g., Monday, Jan. 6, 2020) at a first time (e.g., 10:00 PM), that can be referred to as the current evening, when the user first enters a bed with the intention of going to sleep (e.g., not if the user intends to first watch television or play with a smart phone before going to sleep, etc.), and ends on a second date (e.g., Tuesday, Jan. 7, 2020) at a second time (e.g., 7:00 AM), that can be referred to as the next morning, when the user first exits the bed with the intention of not going back to sleep that next morning.

In some implementations, the user can manually define the beginning of a sleep session and/or manually terminate a sleep session. For example, the user can select (e.g., by clicking or tapping) one or more user-selectable element that is displayed on the display device 172 of the user device 170 (FIG. 1) to manually initiate or terminate the sleep session.

Generally, the sleep session includes any point in time after the user 210 has laid or sat down in the bed 230 (or another area or object on which they intend to sleep), and has turned on the respiratory therapy device 122 and donned the user interface 124. The sleep session can thus include time periods (i) when the user 210 is using the CPAP system but before the user 210 attempts to fall asleep (for example when the user 210 lays in the bed 230 reading a book); (ii) when the user 210 begins trying to fall asleep but is still awake; (iii) when the user 210 is in a light sleep (also referred to as stage 1 and stage 2 of non-rapid eye movement (NREM) sleep); (iv) when the user 210 is in a deep sleep (also referred to as slow-wave sleep, SWS, or stage 3 of NREM sleep); (v) when the user 210 is in rapid eye movement (REM) sleep; (vi) when the user 210 is periodically awake between light sleep, deep sleep, or REM sleep; or (vii) when the user 210 wakes up and does not fall back asleep.

The sleep session is generally defined as ending once the user 210 removes the user interface 124, turns off the respiratory therapy device 122, and gets out of bed 230. In some implementations, the sleep session can include additional periods of time, or can be limited to only some of the above-disclosed time periods. For example, the sleep session can be defined to encompass a period of time beginning when the respiratory therapy device 122 begins supplying the pressurized air to the airway or the user 210, ending when the respiratory therapy device 122 stops supplying the pressurized air to the airway of the user 210, and including some or all of the time points in between, when the user 210 is asleep or awake.

Figure 3:
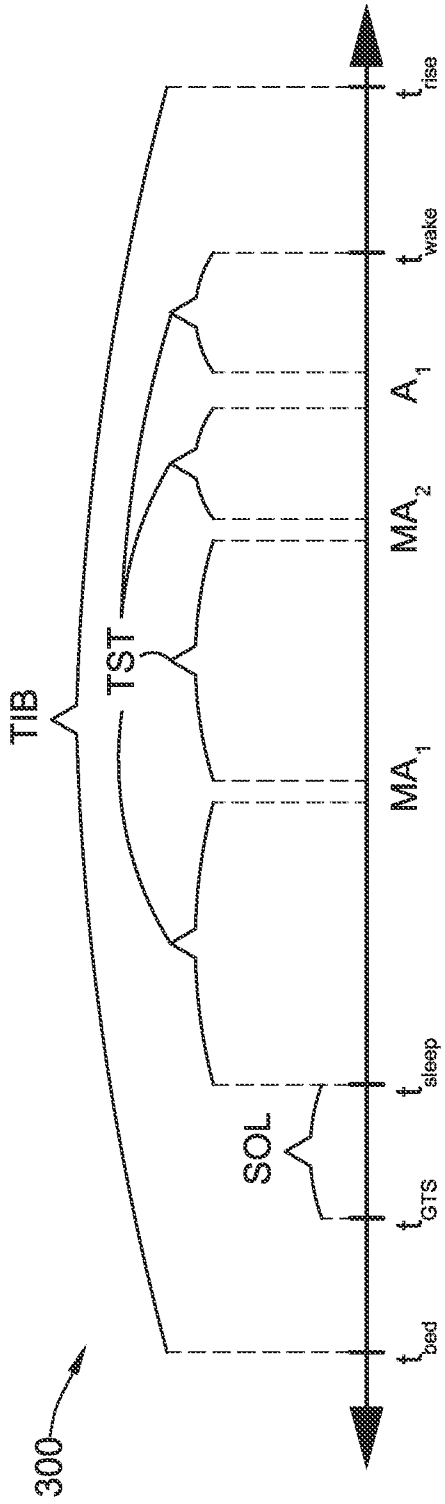
FIG. 3 illustrates an exemplary timeline for a sleep session, according to some implementations of the present disclosure.

Referring to FIG. 3, an exemplary timeline 300 for a sleep session is illustrated. The timeline 300 includes an enter bed time ($t_{bed}$), a go-to-sleep time ($t_{GTS}$), an initial sleep time ($t_{sleep}$), a first micro-awakening $MA_1$, a second micro-awakening $MA_2$, an awakening A, a wake-up time ($t_{wake}$), and a rising time ($t_{rise}$).

The enter bed time $t_{bed}$ is associated with the time that the user initially enters the bed (e.g., bed 230 in FIG. 2) prior to falling asleep (e.g., when the user lies down or sits in the bed). The enter bed time $t_{bed}$ can be identified based on a bed threshold duration to distinguish between times when the user enters the bed for sleep and when the user enters the bed for other reasons (e.g., to watch TV). For example, the bed threshold duration can be at least about 10 minutes, at least about 20 minutes, at least about 30 minutes, at least about 45 minutes, at least about 1 hour, at least about 2 hours, etc. While the enter bed time $t_{bed}$ is described herein in reference to a bed, more generally, the enter time $t_{bed}$ can refer to the time the user initially enters any location for sleeping (e.g., a couch, a chair, a sleeping bag, etc.).

The go-to-sleep time (GTS) is associated with the time that the user initially attempts to fall asleep after entering the bed ($t_{bed}$). For example, after entering the bed, the user may engage in one or more activities to wind down prior to trying to sleep (e.g., reading, watching TV, listening to music, using the user device 170, etc.). The initial sleep time ($t_{sleep}$) is the time that the user initially falls asleep. For example, the initial sleep time ($t_{sleep}$) can be the time that the user initially enters the first non-REM sleep stage.

The wake-up time $t_{wake}$ is the time associated with the time when the user wakes up without going back to sleep (e.g., as opposed to the user waking up in the middle of the night and going back to sleep). The user may experience one of more unconscious microawakenings (e.g., microawakenings $MA_1$ and $MA_2$) having a short duration (e.g., 5 seconds, 10 seconds, 30 seconds, 1 minute, etc.) after initially falling asleep. In contrast to the wake-up time $t_{wake}$, the user goes back to sleep after each of the microawakenings $MA_1$ and $MA_2$. Similarly, the user may have one or more conscious awakenings (e.g., awakening A) after initially falling asleep (e.g., getting up to go to the bathroom, attending to children or pets, sleep walking, etc.). However, the user goes back to sleep after the awakening A. Thus, the wake-up time $t_{wake}$ can be defined, for example, based on a wake threshold duration (e.g., the user is awake for at least 15 minutes, at least 20 minutes, at least 30 minutes, at least 1 hour, etc.).

Similarly, the rising time $t_{rise}$ is associated with the time when the user exits the bed and stays out of the bed with the intent to end the sleep session (e.g., as opposed to the user getting up during the night to go to the bathroom, to attend to children or pets, sleep walking, etc.). In other words, the rising time $t_{rise}$ is the time when the user last leaves the bed without returning to the bed until a next sleep session (e.g., the following evening). Thus, the rising time $t_{rise}$ can be defined, for example, based on a rise threshold duration (e.g., the user has left the bed for at least 15 minutes, at least 20 minutes, at least 30 minutes, at least 1 hour, etc.). The enter bed time $t_{bed}$ time for a second, subsequent sleep session can also be defined based on a rise threshold duration (e.g., the user has left the bed for at least 4 hours, at least 6 hours, at least 8 hours, at least 12 hours, etc.).

As described above, the user may wake up and get out of bed one more times during the night between the initial $t_{bed}$ and the final $t_{rise}$. In some implementations, the final wake-up time $t_{wake}$ and/or the final rising time $t_{rise}$ that are identified or determined based on a predetermined threshold duration of time subsequent to an event (e.g., falling asleep or leaving the bed). Such a threshold duration can be customized for the user. For a standard user which goes to bed in the evening, then wakes up and goes out of bed in the morning any period (between the user waking up ($t_{wake}$) or raising up ($t_{rise}$), and the user either going to bed ($t_{bed}$), going to sleep ($t_{GTS}$) or falling asleep ($t_{sleep}$) of between about 12 and about 18 hours can be used. For users that spend longer periods of time in bed, shorter threshold periods may be used (e.g., between about 8 hours and about 14 hours). The threshold period may be initially selected and/or later adjusted based on the system monitoring the user's sleep behavior.

The total time in bed (TIB) is the duration of time between the time enter bed time $t_{bed}$ and the rising time $t_{rise}$. The total sleep time (TST) is associated with the duration between the initial sleep time and the wake-up time, excluding any conscious or unconscious awakenings and/or micro-awakenings therebetween. Generally, the total sleep time (TST) will be shorter than the total time in bed (TIB) (e.g., one minute short, ten minutes shorter, one hour shorter, etc.). For example, referring to the timeline 300 of FIG. 3, the total sleep time (TST) spans between the initial sleep time $t_{sleep}$ and the wake-up time $t_{wake}$, but excludes the duration of the first micro-awakening $MA_1$, the second micro-awakening $MA_2$, and the awakening A. As shown, in this example, the total sleep time (TST) is shorter than the total time in bed (TIB).

In some implementations, the total sleep time (TST) can be defined as a persistent total sleep time (PTST). In such implementations, the persistent total sleep time excludes a predetermined initial portion or period of the first non-REM stage (e.g., light sleep stage). For example, the predetermined initial portion can be between about 30 seconds and about 20 minutes, between about 1 minute and about 10 minutes, between about 3 minutes and about 5 minutes, etc. The persistent total sleep time is a measure of sustained sleep, and smooths the sleep-wake hypnogram. For example, when the user is initially falling asleep, the user may be in the first non-REM stage for a very short time (e.g., about 30 seconds), then back into the wakefulness stage for a short period (e.g., one minute), and then goes back to the first non-REM stage. In this example, the persistent total sleep time excludes the first instance (e.g., about 30 seconds) of the first non-REM stage.

In some implementations, the sleep session is defined as starting at the enter bed time ($t_{bed}$) and ending at the rising time ($t_{rise}$), i.e., the sleep session is defined as the total time in bed (TIB). In some implementations, a sleep session is defined as starting at the initial sleep time ($t_{sleep}$) and ending at the wake-up time ($t_{wake}$). In some implementations, the sleep session is defined as the total sleep time (TST). In some implementations, a sleep session is defined as starting at the go-to-sleep time ($t_{GTS}$) and ending at the wake-up time ($t_{wake}$). In some implementations, a sleep session is defined as starting at the go-to-sleep time ($t_{GTS}$) and ending at the rising time ($t_{rise}$). In some implementations, a sleep session is defined as starting at the enter bed time ($t_{bed}$) and ending at the wake-up time ($t_{wake}$). In some implementations, a sleep session is defined as starting at the initial sleep time ($t_{sleep}$) and ending at the rising time ($t_{rise}$).

Generally, the sleep session can include any point in time after the user 210 has laid or sat down in the bed 230 (or another area or object on which they intend to sleep), and has turned on the respiratory therapy device 122 and donned the user interface 124. The sleep session can thus include time periods (i) when the user 210 is using the CPAP system but before the user 210 attempts to fall asleep (for example when the user 210 lays in the bed 230 reading a book); (ii) when the user 210 begins trying to fall asleep but is still awake; (iii) when the user 210 is in a light sleep (also referred to as stage 1 and stage 2 of non-rapid eye movement (NREM) sleep); (iv) when the user 210 is in a deep sleep (also referred to as slow-wave sleep, SWS, or stage 3 of NREM sleep); (v) when the user 210 is in rapid eye movement (REM) sleep; (vi) when the user 210 is periodically awake between light sleep, deep sleep, or REM sleep; or (vii) when the user 210 wakes up and does not fall back asleep.

The sleep session can be generally defined as ending once the user 210 removes the user interface 124, turns off the respiratory therapy device 122, and gets out of bed 230. In some implementations, the sleep session can include additional periods of time, or can be limited to only some of the above-disclosed time periods. For example, the sleep session can be defined to encompass a period of time beginning when the respiratory therapy device 122 begins supplying the pressurized air to the airway or the user 210, ending when the respiratory therapy device 122 stops supplying the pressurized air to the airway of the user 210, and including some or all of the time points in between, when the user 210 is asleep or awake.

Figure 4:
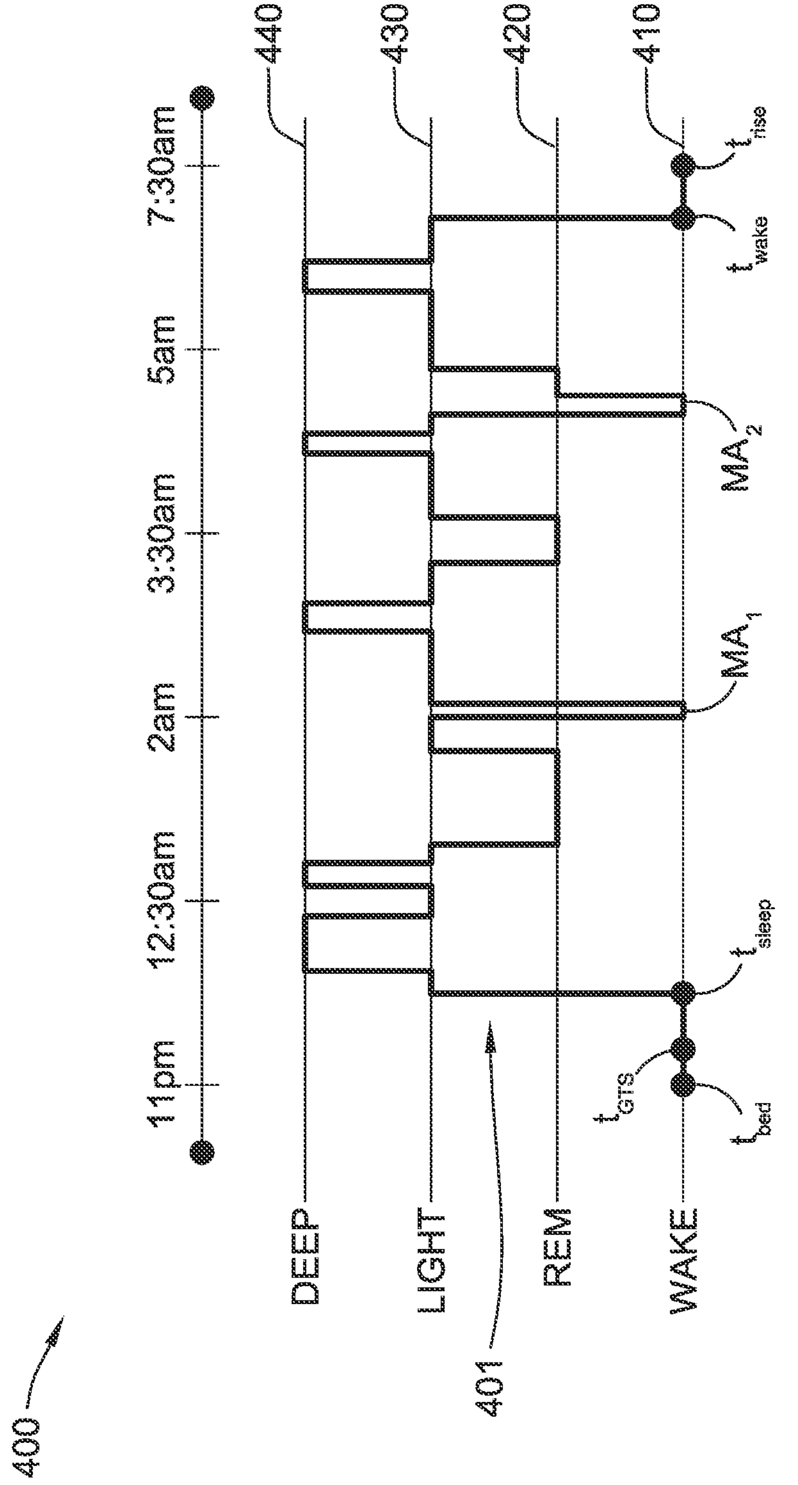
FIG. 4 illustrates an exemplary hypnogram associated with the sleep session of FIG. 3, according to some implementations of the present disclosure.

Referring to FIG. 4, an exemplary hypnogram 400 corresponding to the timeline 300 (FIG. 3), according to some implementations, is illustrated. As shown, the hypnogram 400 includes a sleep-wake signal 401, a wakefulness stage axis 410, a REM stage axis 420, a light sleep stage axis 430, and a deep sleep stage axis 440. The intersection between the sleep-wake signal 401 and one of the axes 410-440 is indicative of the sleep stage at any given time during the sleep session.

The sleep-wake signal 401 can be generated based on physiological data associated with the user (e.g., generated by one or more of the sensors 130 described herein). The sleep-wake signal can be indicative of one or more sleep states, including wakefulness, relaxed wakefulness, micro-awakenings, a REM stage, a first non-REM stage, a second non-REM stage, a third non-REM stage, or any combination thereof. In some implementations, one or more of the first non-REM stage, the second non-REM stage, and the third non-REM stage can be grouped together and categorized as a light sleep stage or a deep sleep stage. For example, the light sleep stage can include the first non-REM stage and the deep sleep stage can include the second non-REM stage and the third non-REM stage. While the hypnogram 400 is shown in FIG. 4 as including the light sleep stage axis 430 and the deep sleep stage axis 440, in some implementations, the hypnogram 400 can include an axis for each of the first non-REM stage, the second non-REM stage, and the third non-REM stage. In other implementations, the sleep-wake signal can also be indicative of a respiration signal, a respiration rate, an inspiration amplitude, an expiration amplitude, an inspiration-expiration ratio, a number of events per hour, a pattern of events, or any combination thereof. Information describing the sleep-wake signal can be stored in the memory device 114.

The hypnogram 400 can be used to determine one or more sleep-related parameters, such as, for example, a sleep onset latency (SOL), wake-after-sleep onset (WASO), a sleep efficiency (SE), a sleep fragmentation index, sleep blocks, or any combination thereof.

The sleep onset latency (SOL) is defined as the time between the go-to-sleep time ($t_{GTS}$) and the initial sleep time ($t_{sleep}$). In other words, the sleep onset latency is indicative of the time that it took the user to actually fall asleep after initially attempting to fall asleep. In some implementations, the sleep onset latency is defined as a persistent sleep onset latency (PSOL). The persistent sleep onset latency differs from the sleep onset latency in that the persistent sleep onset latency is defined as the duration time between the go-to-sleep time and a predetermined amount of sustained sleep. In some implementations, the predetermined amount of sustained sleep can include, for example, at least 10 minutes of sleep within the second non-REM stage, the third non-REM stage, and/or the REM stage with no more than 2 minutes of wakefulness, the first non-REM stage, and/or movement therebetween. In other words, the persistent sleep onset latency requires up to, for example, 8 minutes of sustained sleep within the second non-REM stage, the third non-REM stage, and/or the REM stage. In other implementations, the predetermined amount of sustained sleep can include at least 10 minutes of sleep within the first non-REM stage, the second non-REM stage, the third non-REM stage, and/or the REM stage subsequent to the initial sleep time. In such implementations, the predetermined amount of sustained sleep can exclude any micro-awakenings (e.g., a ten second micro-awakening does not restart the 10-minute period).

The wake-after-sleep onset (WASO) is associated with the total duration of time that the user is awake between the initial sleep time and the wake-up time. Thus, the wake-after-sleep onset includes short and micro-awakenings during the sleep session (e.g., the micro-awakenings $MA_1$ and $MA_2$ shown in FIG. 4), whether conscious or unconscious. In some implementations, the wake-after-sleep onset (WASO) is defined as a persistent wake-after-sleep onset (PWASO) that only includes the total durations of awakenings having a predetermined length (e.g., greater than 10 seconds, greater than 30 seconds, greater than 60 seconds, greater than about 5 minutes, greater than about 10 minutes, etc.)

The sleep efficiency (SE) is determined as a ratio of the total time in bed (TIB) and the total sleep time (TST). For example, if the total time in bed is 8 hours and the total sleep time is 7.5 hours, the sleep efficiency for that sleep session is 93.75%. The sleep efficiency is indicative of the sleep hygiene of the user. For example, if the user enters the bed and spends time engaged in other activities (e.g., watching TV) before sleep, the sleep efficiency will be reduced (e.g., the user is penalized). In some implementations, the sleep efficiency (SE) can be calculated based on the total time in bed (TIB) and the total time that the user is attempting to sleep. In such implementations, the total time that the user is attempting to sleep is defined as the duration between the go-to-sleep (GTS) time and the rising time described herein. For example, if the total sleep time is 8 hours (e.g., between 11 PM and 7 AM), the go-to-sleep time is 10:45 PM, and the rising time is 7:15 AM, in such implementations, the sleep efficiency parameter is calculated as about 94%.

The fragmentation index is determined based at least in part on the number of awakenings during the sleep session. For example, if the user had two micro-awakenings (e.g., micro-awakening $MA_1$ and micro-awakening $MA_2$ shown in FIG. 4), the fragmentation index can be expressed as 2. In some implementations, the fragmentation index is scaled between a predetermined range of integers (e.g., between 0 and 10).

The sleep blocks are associated with a transition between any stage of sleep (e.g., the first non-REM stage, the second non-REM stage, the third non-REM stage, and/or the REM) and the wakefulness stage. The sleep blocks can be calculated at a resolution of, for example, 30 seconds.

In some implementations, the systems and methods described herein can include generating or analyzing a hypnogram including a sleep-wake signal to determine or identify the enter bed time ($t_{bed}$), the go-to-sleep time ($t_{GTS}$), the initial sleep time ($t_{sleep}$), one or more first micro-awakenings (e.g., $MA_1$ and $MA_2$), the wake-up time ($t_{wake}$), the rising time ($t_{rise}$), or any combination thereof based at least in part on the sleep-wake signal of a hypnogram.

In other implementations, one or more of the sensors 130 can be used to determine or identify the enter bed time ($t_{bed}$), the go-to-sleep time ($t_{GTS}$), the initial sleep time ($t_{sleep}$), one or more first micro-awakenings (e.g., $MA_1$ and $MA_2$), the wake-up time ($t_{wake}$), the rising time ($t_{rise}$), or any combination thereof, which in turn define the sleep session. For example, the enter bed time $t_{bed}$ can be determined based on, for example, data generated by the motion sensor 138, the microphone 140, the camera 150, or any combination thereof. The go-to-sleep time can be determined based on, for example, data from the motion sensor 138 (e.g., data indicative of no movement by the user), data from the camera 150 (e.g., data indicative of no movement by the user and/or that the user has turned off the lights) data from the microphone 140 (e.g., data indicative of the using turning off a TV), data from the user device 170 (e.g., data indicative of the user no longer using the user device 170), data from the pressure sensor 132 and/or the flow rate sensor 134 (e.g., data indicative of the user turning on the respiratory therapy device 122, data indicative of the user donning the user interface 124, etc.), or any combination thereof.

Figure 5:
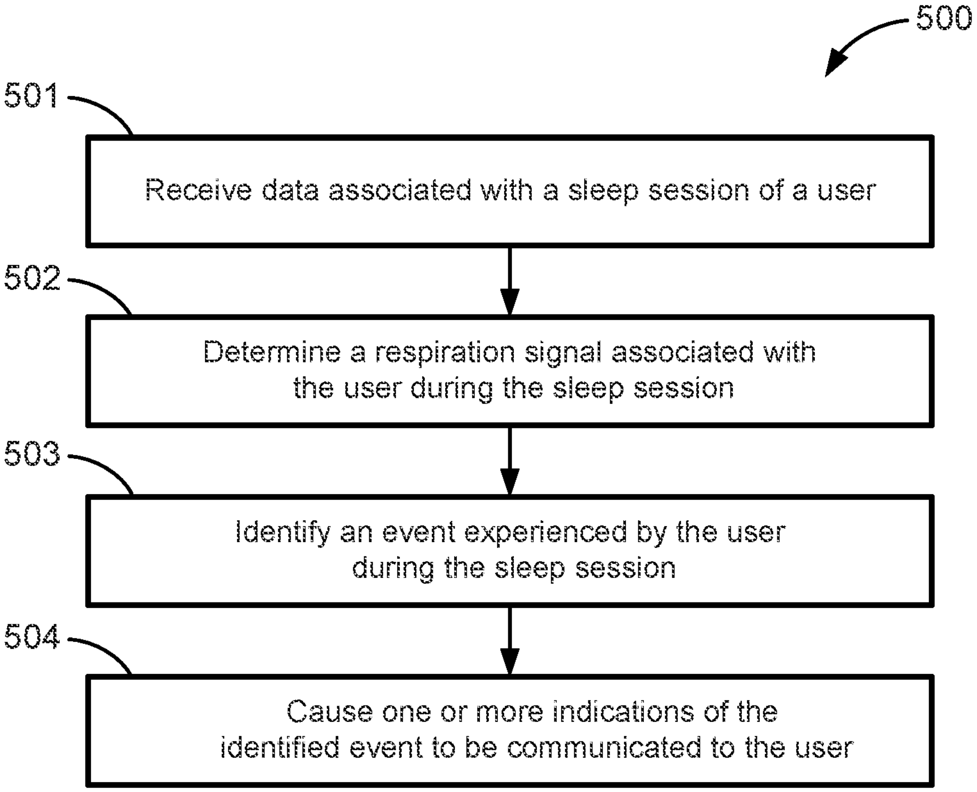
FIG. 5 is a process flow diagram for a method for identifying an event experienced by a user during a sleep session, according to some implementations of the present disclosure.

Referring to FIG. 5, a method 500 for identifying an event experienced by a user during a sleep session and communicating a visual and/or audio indication of that event to the user subsequent to the sleep session according to some implementations of the present disclosure is illustrated. One or more steps of the method 500 can be implemented using any element or aspect of the system 100 (FIGS. 1-2) described herein.

Step 501 of the method 500 includes generating and/or receiving data associated with a sleep session of a user. The data can include, for example, respiration data associated with the user, audio data associated with the user, or both the respiration data and the audio data. The respiration data is indicative of respiration of the user (e.g., a respiration rate, a respiration rate variability, a tidal volume, an inspiration amplitude, an expiration amplitude, and/or an inspiration-expiration ratio) during at least a portion of the sleep session (e.g., at least 10% of the sleep session, at least 50% of the sleep session, 75% of the sleep session, at least 90% of the sleep session, etc.). The audio data is reproducible as one or more sounds recorded during the sleep session (e.g., snoring, choking, breathing, a pause in breathing, labored breathing, etc.).

In some implementations, the respiration data is generated by a first one of the one or more sensors 130 and the audio data is generated by a second one of the one or more sensors 130. For example, the respiration data can be generated by the pressure sensor 132 and/or flow rate sensor 134, and the audio data can be generated by the microphone 140. In this example, the pressure sensor 130 and/or the flow rate sensor 134 can be coupled to or integrated in any component or aspect of the respiratory therapy system 120 described herein, while the microphone 140 can be coupled to or integrated in the user device 170. In other implementations, the respiration data and the audio data are generated by the same one(s) of the one or more sensors 130. In such implementations, the respiration data and the audio data can be generated by, for example, the acoustic sensor 141. The data can be received from the one or more sensors 130 by, for example, the electronic interface 119 and/or the user device 170 (FIG. 1) described herein.

The respiration data and the audio data can be time-stamped such that a portion of the audio data can be associated with a corresponding portion of the respiration data that is associated with the same time interval. For example, as described below, if the user experienced an event during a time interval during the sleep session, the associated audio can be identified based on the timestamp information.

Step 502 of the method 500 includes determining a respiration signal associated with the user during the sleep session based at least in part on the data received during step 501. The respiration signal can be determined based at least in part on the respiration data, the audio data, or both. For example, the control system 110 can analyze the data (e.g., that is stored in the memory device 114) received during step 501 to determine the respiration signal associated with the user during the sleep session. Information associated with and/or describing the determined respiration signal can be stored in the memory device 114 (FIG. 1), for example.

Figure 6:
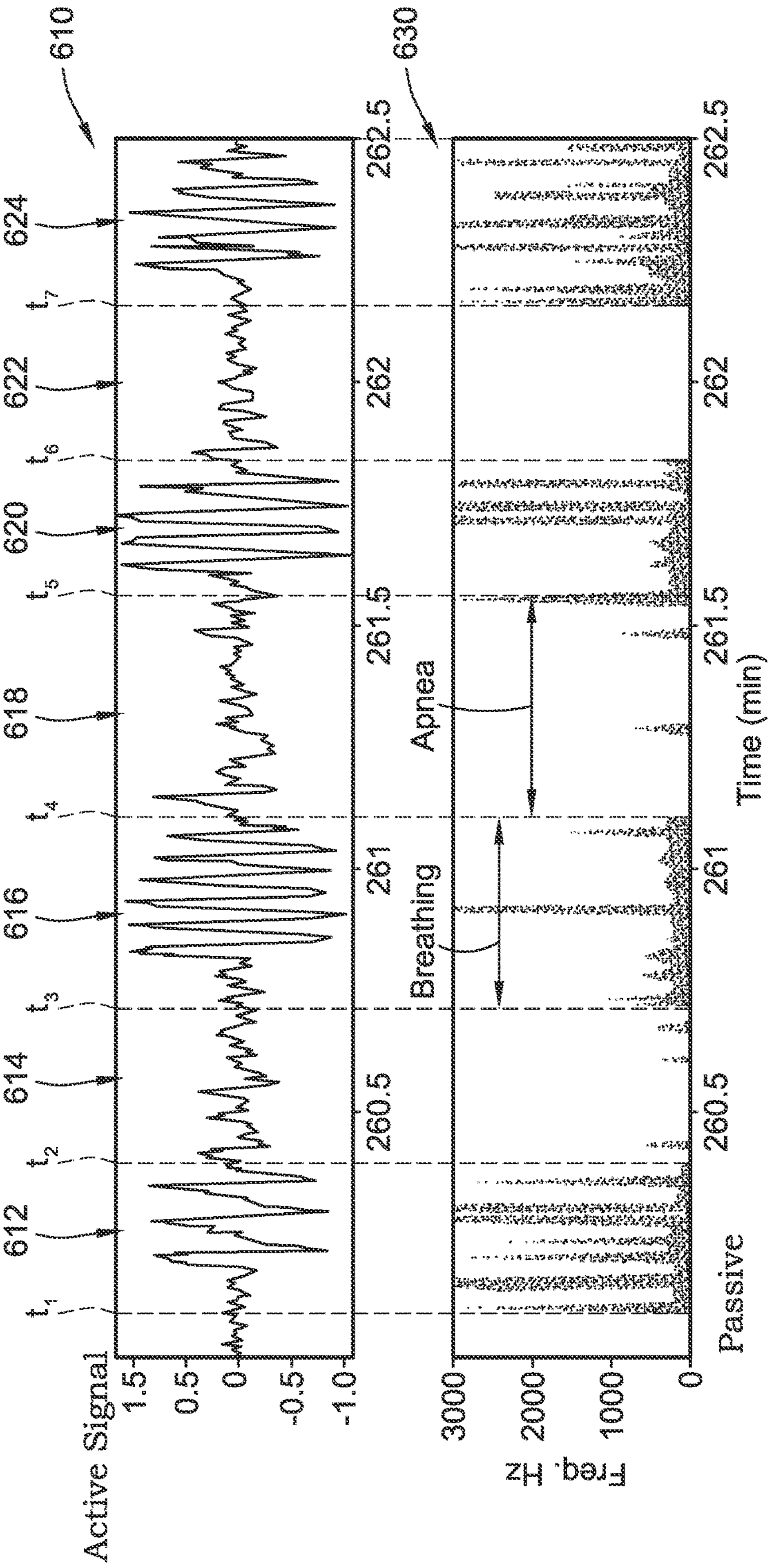
FIG. 6 illustrates an exemplary respiration signal and an exemplary audio signal associated with a user during a sleep session, according to some implementations of the present disclosure.

Referring to FIG. 6, an exemplary respiration signal 610 associated with a user during a portion of a sleep session is illustrated. The y-axis represents the amplitude of the respiration signal 610 and the x-axis represents time (e.g., in minutes and/or seconds). The respiration signal 610 includes a plurality of inhalation portions and a plurality of expiration portions. Each inhalation portion corresponds to the user breathing in (inspiration) and each exhalation portion corresponds to the user breathing out (expiration). In some implementations, the integral of one of the inhalation portions of the respiration signal 610 is equal to the integral of a corresponding one of the exhalation portions of the respiration signal 610. In the example shown in FIG. 6, the respiration signal 610 includes a first portion 612 between time $t_1$ and time $t_2$, a second portion 614 between time $t_2$ and time $t_3$, a third portion 616 between time $t_3$ and time $t_4$, a fourth portion 618 between time $t_4$ and time $t_3$, a fifth portion 620 between time $t_5$ and time $t_6$, a sixth portion 622 between time $t_6$ and time $t_7$, and a seventh portion 624 between time $t_7$ and time $t_8$. The respiration signal 610 can be indicative of, among other things, one or more events experienced by the user during the portion of the first sleep session.

In some implementations, step 502 of the method 500 also includes determining an audio signal associated with the sleep session based at least in part on the audio data received during step 501. Referring to FIG. 6, an exemplary audio signal 630 associated with the user during a portion of a sleep session is illustrated. The y-axis represents the frequency of the audio signal 630 and the x-axis represents time (e.g., in minutes). As illustrated in FIG. 6, the audio signal 630 generally corresponds to the respiration signal 610. In particular, the frequency of the audio signal 630 generally corresponds with (e.g., is correlated with) the amplitude of the respiration signal 610. For example, the average amplitude of the first portion 612 of the respiration signal 610 between time $t_1$ and $t_2$ is greater than the average amplitude of the second portion 614 of the audio signal 610 between time $t_2$ and $t_3$ (e.g., which is indicative of a pause in breathing between time $t_2$ and $t_3$). Likewise, the average frequency of the audio signal 630 between time $t_1$ and $t_2$ is greater than the average frequency of the audio signal 630 between time $t_2$ and $t_3$ (e.g., which is indicative of a pause in breathing between time $t_2$ and $t_3$). The audio data (step 501) and/or the determined audio signal (step 502) can be used to aid in identifying an event experienced by the user during a sleep session.

Step 503 of the method 503 (FIG. 5) includes identifying one or more events experienced by the user during the sleep session. For example, the control system 110 can analyze the data (e.g., that is stored in the memory device 114) received during step 501 and/or the determined the respiration signal (step 502) to identify event(s) experienced by the user during the sleep session. The identified event(s) can be snoring, an apnea, a central apnea, an obstructive apnea or obstructive sleep apnea (OSA), a mixed apnea, a hypopnea, a restless leg, a sleeping disorder, choking, labored breathing, an asthma attack, an epileptic episode, a seizure, or any combination thereof.

In some implementations, step 503 includes identifying an event based at least in part on the received respiration data (step 501) and/or the determined respiration signal (step 502). For example, referring to FIG. 6, the first portion 612, the third portion 616, the fifth portion 620, and the seventh portion 624 of the respiration signal 610 are associated with normal breathing (e.g., one or more inhalations and one or more exhalations). The second portion 614 is associated with a first event, the fourth portion 618 is associated with a second event, and the sixth portion 620 is associated with a third event. In this particular example, the first event, second event, and third event are obstructive sleep apnea (OSA) events. These events can be identified within the respiration signal 610, for example, based on the relative amplitude of the respiration signal 610 in the first portion 612, the third portion 616, the fifth portion 620, and the seventh portion 624 relative to the second portion 614, the fourth portion 618, and the sixth portion 620. As another example, each event in the respiration signal 610 can be identified by comparing the amplitude of the respiration signal 610 to a predetermined threshold. For example, an average of the amplitude of the respiration signal 610 for a predetermined time period or sampling rate (e.g., 1 second, 3 seconds, 5 seconds, 10 seconds, 30 seconds, 1 minute, 3 minutes, etc.) can be compared to the predetermined threshold to identify one or more events during the sleep session.

In some implementations, step 503 includes identifying an event based at least in part on at least a portion of the respiration data and at least a portion of the audio data received during step 501. In such implementations, the audio data can be analyzed (e.g., by the control system 110) to detect or measure respiration or breathing of the user. The audio data can also be analyzed to detect or identify a reduction or decrease in the frequency and/or amplitude of the audio, which can be indicative of a temporary cessation or pause in breathing due to an obstructive sleep apnea (OSA) event, for example. Thus, the event can be identified responsive to determining that the frequency and/or amplitude of the audio data falls below a predetermined threshold for a predetermination duration (e.g., between about 10 seconds and about 45 seconds, between about 15 seconds and about 30 seconds, etc.).

A reduction in the audio amplitude, however, can be attributable to a change in the ambient noise level in the room in which the user is sleeping rather than the user experiencing an event (e.g., a pause in breathing). Environmental factors that can affect the ambient noise include, for example, ventilation or air flow (e.g., from an HVAC system, a fan, a humidifier, a dehumidifier, air purifier, etc.), household appliances (e.g., television, speakers, etc.), noise outside of the room (e.g., roommates, neighbors, traffic, etc.), or the like. Thus, step 503 can include filtering ambient noise(s) from the audio data to identify the respiration and/or breathing of the user. Ambient noise can be filtered, for example, using a machine learning algorithm.

Further, in such implementations where step 503 includes identifying an event based at least in part on the audio data, step 503 can also include determining a position and/or orientation of the user relative to the one of the one or more sensors 130 that is generating the audio data (e.g., the microphone 140). For instance, the user may turn or move away from the sensor generating the audio data during the sleep session, which may cause a corresponding reduction of the audio amplitude. However, even as the amplitude of the audio signal may be reduced based on the position of the user relative to the sensor, the relative changes in the amplitude of the audio signal in response to an event (e.g., OSA event) are generally the same. Thus, the determined position and/or orientation of the user can be used to modify any of the predetermined audio thresholds described herein.

In some implementations, step 503 includes identifying event(s) using a machine learning algorithm that is trained (e.g., using supervised or unsupervised learning techniques) to receive the respiration data (step 501) and/or the determined respiration signal (step 502) and output an identification of one or more events. In such implementations, the machine learning algorithm can also be trained to additionally receive as an input the audio data (step 501) and/or the determined audio signal (step 502) and output the identification of one or more events.

In some implementations, step 503 of the method 500 also includes determining one or more sleep-related parameters associated with the user during the sleep session based at least in part on the received data (step 501). The one or more sleep-related parameters, for example, an apnea-hypopnea index (AHI), a number of events per hour, a pattern of events, a total sleep time, a total time in bed, a wake-up time, a rising time, a hypnogram, a total light sleep time, a total deep sleep time, a total REM sleep time, a number of awakenings, a sleep-onset latency, or any combination thereof. In some implementations, the one or more sleep-related parameters can include a sleep score, such as the ones described in International Publication No. WO 2015/006364, which is hereby incorporated by reference herein in its entirety. The one or more sleep-related parameters can include any number of sleep-related parameters (e.g., 1 sleep-related parameter, 2 sleep-related parameters, 5 sleep-related parameters, 50 sleep-related parameters, etc.).

Step 504 of the method 500 (FIG. 5) includes causing one or more indications of an identified event (step 503) to be communicated to the user subsequent to the sleep session. The one or more indications can include a visual indication (e.g., alphanumeric text, images, videos, etc.) and/or an audio indication (e.g., a recording of the user's breathing (or temporary lack thereof) during the sleep session, snoring, etc.). The one or more indications can be communicated to the user using, for example, the user device 170 (e.g., using the display device 172 of the user device 170 and/or the speaker 142). The one or more indications generally describe the identified event (step 503) and/or otherwise communicate information associated with or describing the identified event to the user.

In some implementations, step 504 occurs responsive to a determination, made based at least in part on the received data (step 501), that an apnea-hypopnea index (AHI) for the sleep session that is equal to or greater than a predetermined threshold value. As described above, the AHI is calculated by dividing the number of apnea and/or hypopnea events experienced by the user during the sleep session by the total number of hours of sleep in the sleep session. In such implementations, the one or more indications are only communicated to the user if the AHI is equal to or greater than the predetermined threshold value. The predetermined threshold value can be, for example, an AHI of about 15.

In some implementations, step 503 includes identifying a single event during a portion of the sleep session. In other implementations, step 503 includes identifying a plurality of events during all or a portion of the sleep session. For example, referring to the exemplary respiration signal 610 of FIG. 6, three separate events were identified: a first event occurring in the second portion 614, a second event occurring in the fourth portion 618, and a third event occurring in the sixth portion 622. Step 504 includes causing one or more indications for a single identified event (e.g., as opposed to multiple events) to be communicated to the user, even if multiple events are identified during step 503.

Thus, in implementations where multiple events are identified during step 503, step 504 includes selecting one of a plurality of identified events and communicating one or more indications for that selected event. Generally, the one of the plurality of identified event is selected so that the one or more indications associated with that event are most likely to induce a behavioral response by the user (e.g., continue to use their respiratory therapy system, seek diagnosis and/or treatment, change bedtime habits, etc.). In some implementations, a first one of a plurality of events can be selected by comparing each of the plurality of events to one another. For example, a first one of the plurality of events can be selected responsive to determining that the first one of the plurality of events is associated with a change in a frequency and/or amplitude in the audio data/signal (e.g., relative to a section of the signal indicative of normal breathing) that is greater than the change in frequency and/or amplitude for all of the others of the plurality of events. In another example, a first one of the plurality of events can be selected responsive to determining that the first one of the plurality of events is associated with a duration where the user stopped breathing (e.g., as indicated by silence in the audio data) that is greater than the duration where the user stopped breathing for all of the others of the plurality of events. In some implementations, selecting one of a plurality of identified events includes using a linear regression algorithm. The linear regression algorithm can be used, for example, to determine a percentage likelihood for each identified event being an actual obstructive sleep apnea (OSA) event.

Figure 7:
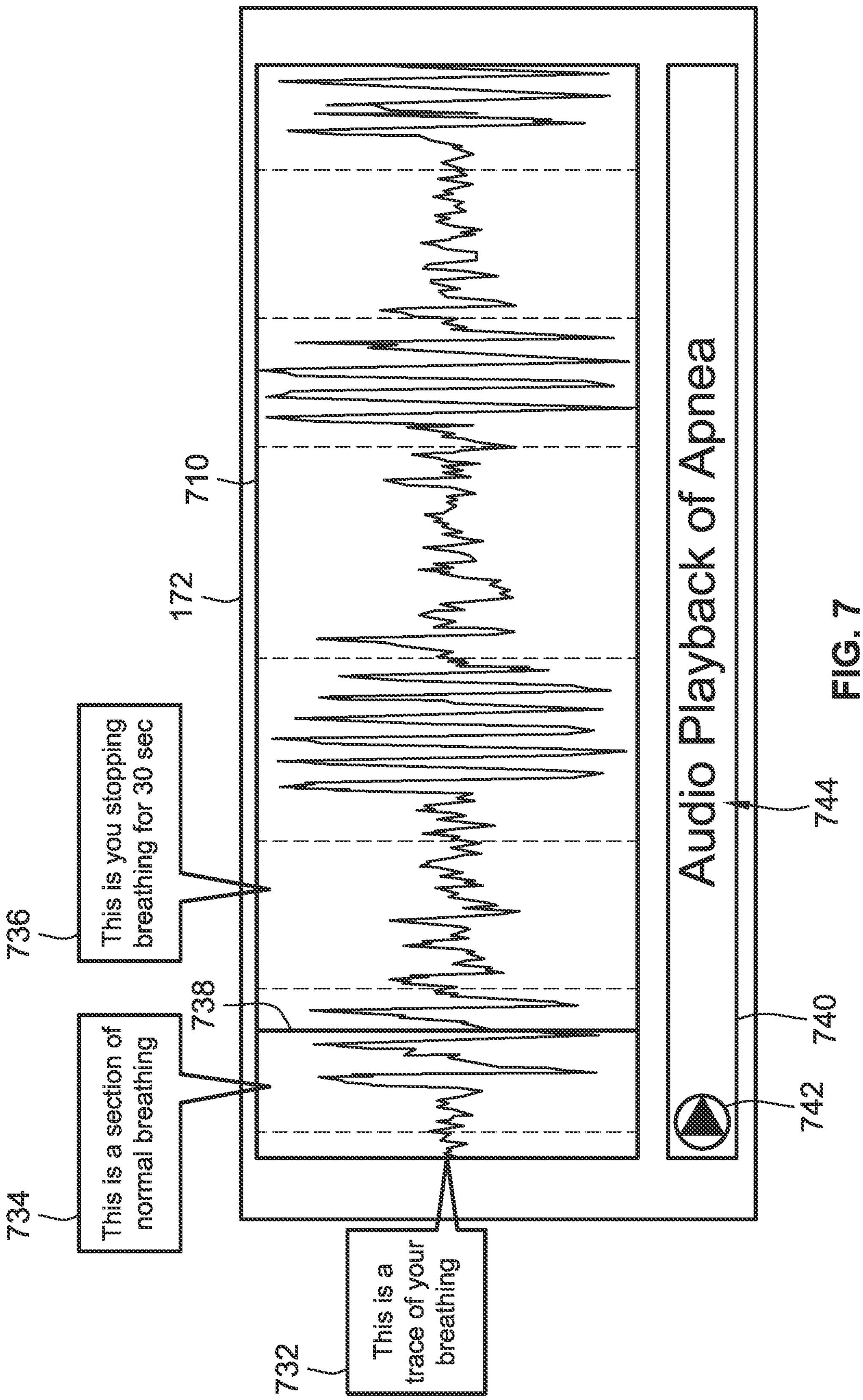
FIG. 7 illustrates an exemplary graphical representation of a portion of a respiration signal and an event indication, according to some implementations of the present disclosure.

The one or more indications that are communicated to the user during step 504 can include, for example, a graphical representation, an event indication, an audio indication, or any combination thereof. Referring to FIG. 7, a graphical representation 710 of at least a portion of the determined respiration signal (step 502) is displayed on the display device 172 of the user device 170 (FIG. 1) described herein. As shown by a comparison of FIG. 6 and FIG. 7, the respiration signal corresponding to the graphical representation 710 is the same as, or similar to, a portion of the determined respiration signal 610 (FIG. 6) described above.

Still referring to FIG. 7, a plurality of indications 732-740 are also displayed on the display device 172 simultaneously with the graphical representation 710. Each of the indications 732-740 can generally include, for example, alphanumeric text, symbols, images, graphics, color(s), or any combination thereof. The indications 732-740 can be displayed such that one or more of the indications 732-740 is partially overlaid on a portion of the graphical representation 710, fully overlaid on a portion of the graphical representation 710, positioned generally adjacent to or spaced from the graphical representation 710.

A first indication 732 generally provides information explaining or describing the graphical representation 710 of the respiration signal to aid the user in understanding and/or interpreting the displayed graphical representation 710. For example, the first indication 732 can include alphanumeric text describing the graphical representation 710 (e.g., "This is a trace of your breathing").

A second indication 734 generally provides information associated with a first portion of the respiration signal illustrated in the graphical representation 710. More specifically, the second indication 734 generally aids in identifying a portion of the respiration signal in the graphical representation 710 where the user did not experience an event (e.g., using alphanumeric text stating: "This is a section of normal breathing"). Providing information about normal breathing, for example, can aid in emphasizing the identified event to the user.

A third indication 736 generally provides information associated with the identified event and generally aids in identifying that event within the graphical representation 710 of the respiration signal. The third indication 736 can communicate information associated with or describing the identified event to the user (e.g., "This is you stopping breathing for 30 seconds"). In some implementations, the third indication 736 is directly overlaid on or included in the graphical representation 710 to highlight (e.g., using a different color, a box or outline, etc.) the portion of the respiration signal corresponding to the identified event.

A first audio indication 740 generally provides information indicating that the user can listen to audio associated with the identified event corresponding to the third indication 736. The first audio indication 740 includes a user-selectable element 742 and an audio indicator 744. Clicking or tapping the user-selectable element 742 causes a portion of the audio data that includes to the identified event to be communicated to the user (e.g., played via the speaker 142). The portion of the audio data can include the entire identified event and a portion of the respiration signal immediately before and/or immediately after the identified event (e.g., 3 seconds, 5 seconds, 10 seconds, 15 seconds, etc. before and/or after the event). The audio indicator 744 can include alphanumeric text (e.g., "audio playback of sleep apnea") explaining that the user can listen to the audio associated with the identified event.

In some implementations, a playback bar 738 is also displayed on the display device 172 along with the graphical representation 710. In response to a selection of the user-selectable element 742, the playback bar 738 moves along the graphical representation 710 (e.g., in a direction towards the third indication 736) as the audio plays to indicate which portion of the graphical representation 710 that the audio corresponds to. In such implementations, the playback bar 738 can also be selectable or interactive such that the user can fast forward or rewind the audio playback (e.g., by tapping and dragging the playback bar 738 in either direction).

Figure 8:
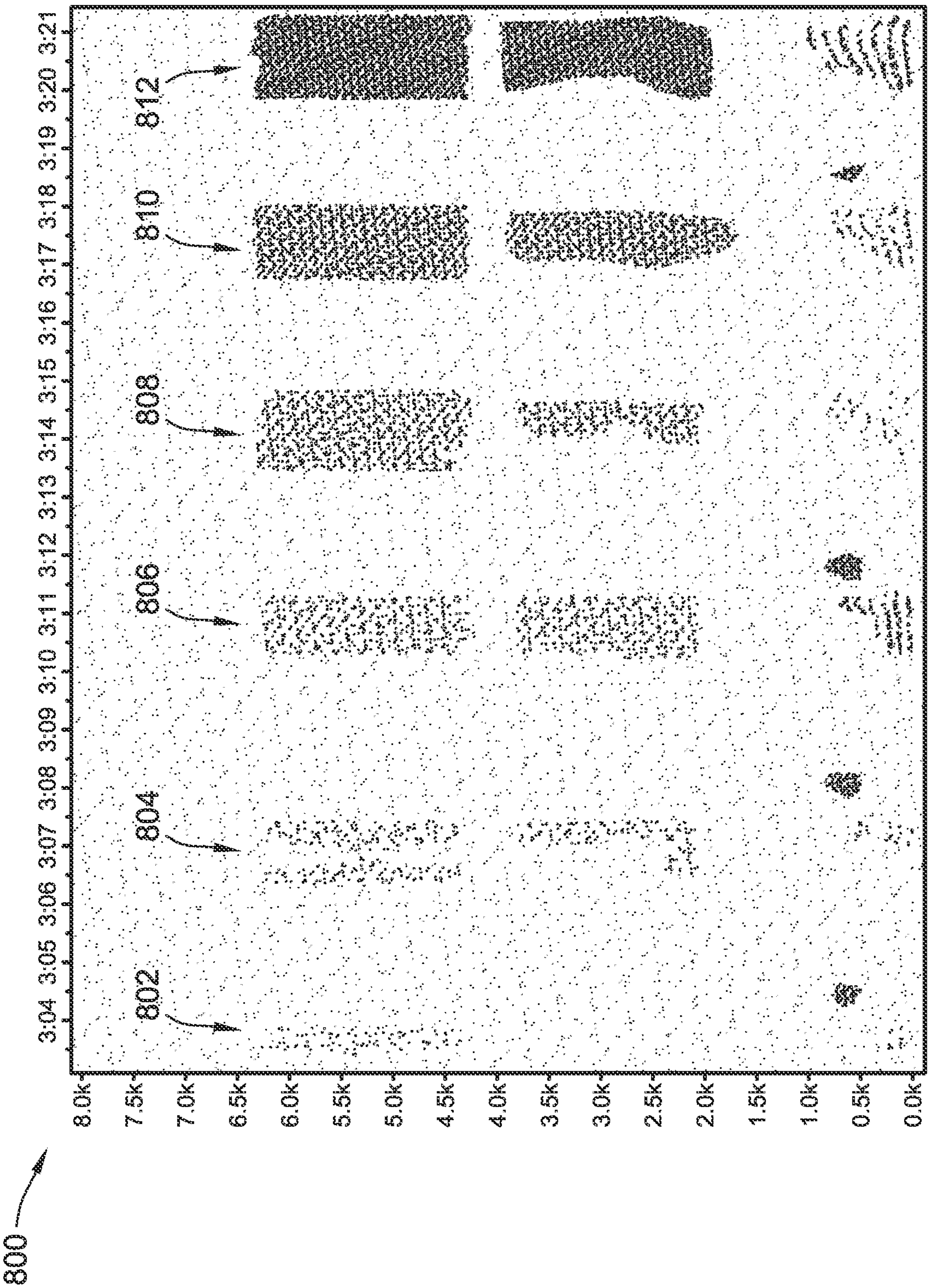
FIG. 8 illustrates an exemplary snoring pattern, according to some implementations of the present disclosure.

Referring to FIG. 8, a plot 800 indicative of a snoring pattern is illustrated. The y-axis corresponds to audio or sound frequency (e.g., measured in kHz) and the x-axis corresponds to time during the sleep session. The snoring pattern includes a series of snores 802-812. In this non-limiting example, the snoring pattern is indicative of increasing respiratory effort (e.g., labored breathing, which can be a risk factor for Sleep Disordered Breathing (SBD)) throughout the series of snores 802-812. The snoring pattern illustrated in this non-limiting example can be referred to as crescendo snoring, wherein successive snores increase in loudness to a crescendo and then reduce in loudness. For example, snores 802-812 progressively increase in loudness to a crescendo, e.g., snore 812, and are then followed by normal breathing or quieter snores, which may resemble snores 802 or 804, for example). In the plot 800, darker lines or shading corresponds to louder sounds (e.g., higher amplitude or intensity of sound is indicated by darker, and optionally thicker, lines or shading) at certain frequencies. The plot 800 can be communicated to the user (e.g., displayed on display device 172) during step 504 alone or in combination with any of the other indications described above. Selection of the plot 800 can be based on the characteristic pattern of crescendo snoring. That is, the snoring event can be selected based on a change in audio amplitude, e.g., a pattern of changes in audio amplitudes, corresponding to crescendo snoring. Additionally, the plot 800 can be communicated to the user (e.g., displayed on display device 172) in combination with communicating the associated audio data to the user (e.g., via the speaker 142) so that the user can hear the snoring reflected within the plot 800.

Some users of the respiratory therapy systems described herein (e.g., CPAP systems) find such systems to be uncomfortable, difficult to use, expensive, and/or aesthetically unappealing. Some users of these systems also may not immediately notice any benefits of use after first beginning therapy. As a result, these users may choose not to use their respiratory therapy system as prescribed (e.g., every night), or even completely discontinue use of the respiratory therapy system altogether. Indeed, some users may altogether avoid seeking diagnosis and/or treatment for symptoms associated with a condition that may require use of a respiration therapy system.

While the sound(s) associated with certain events like snoring, choking, or labored breathing that occur when the user does not use the respiratory therapy system can be quite loud (e.g., from the perspective of the bed partner 220 in FIG. 2), the user cannot hear these noises because they are asleep. The user may be more likely or encouraged to seek treatment, use a respiratory therapy system, and/or adhere to recommended respiratory therapy in the future to reduce or eliminate these events if they could actually hear the sound(s) associated with these events and understand the severity of their symptoms. For example, the time period where the user stops breathing during an OSA event can be between about 15 seconds and about 30 seconds. If the user can listen to this entire relatively lengthy period of silence where they stopped breathing, they would better understand the severity or seriousness of their symptoms and be more likely to seek treatment and/or use the respiratory therapy system as prescribed. Thus, displaying one or more indications of the identified event, along with communicating the associated audio to the user, can aid in encouraging or eliciting a behavioral response by the user, such as using their respiratory therapy system as prescribed, seeking diagnosis and treatment for their symptoms, and/or otherwise changing their sleep habits.

In some implementations, steps 501-504 can be repeated for one or more additional sleep sessions subsequent to the first sleep session (e.g., a third sleep session, a fourth sleep session, a tenth sleep session, a one-hundredth sleep session etc.).

One or more elements or aspects or steps, or any portion(s) thereof, from one or more of any of the claims below can be combined with one or more elements or aspects or steps, or any portion(s) thereof, from one or more of any of the other claims below combinations thereof, to form one or more additional implementations and/or claims of the present disclosure.

While the present disclosure has been described with reference to one or more particular embodiments or implementations, those skilled in the art will recognize that many changes may be made thereto without departing from the spirit and scope of the present disclosure. Each of these implementations and obvious variations thereof is contemplated as falling within the spirit and scope of the present disclosure. It is also contemplated that additional implementations according to aspects of the present disclosure may combine any number of features from any of the implementations described herein.

What is claimed is:

1. A method comprising:

receiving, from one or more sensors, data associated with a sleep session of a user, the data including (i) respiration data associated with the user during at least a portion of the sleep session and (ii) audio data reproducible as one or more sounds associated with the user during at least a portion of the sleep session;

determining a respiration signal associated with the user during the sleep session based, at least in part, on at least a portion of the data;

identifying a plurality of events experienced by the user during the sleep session based, at least in part, on at least a portion of the data;

selecting an apnea event from the plurality of events;

causing a portion of the audio data associated with the selected apnea event to be communicated to the user via a user device; and causing to be communicated to the user via the user device (i) a graphical representation of a portion of the respiration signal, (ii) an event indication that aids in identifying the selected apnea event within the graphical representation of the portion of the respiration signal, and (iii) a playback bar that is time-synchronized to the graphical representation of the portion of the respiration signal, wherein the playback bar traverses the graphical representation along a time axis of the respiration signal to indicate a start, a duration, and an end of the selected apnea event, thereby co-registering playback progress of the portion of the audio data with a temporal extent of the selected apnea event within the graphical representation of the portion of the respiration signal.

2. The method of claim 1, further comprising causing a user-selectable audio element to be displayed via the user device, wherein the causing the portion of the audio data associated with the selected apnea event to be communicated to the user via the user device is in response to a selection of the user-selectable audio element.

3. The method of claim 1, wherein the event indication is at least partially overlaid on or adjacent to the displayed graphical representation of the portion of the respiration signal.

4. The method of claim 1, wherein the event indication includes a graphical indication, alphanumeric text, or both.

5. The method of claim 1, further comprising:

determining one or more sleep-related parameters associated with the sleep session of the user based at least in part on the data; and causing an indication associated with the determined one or more sleep-related parameters to be communicated to the user via the user device.

6. The method of claim 5, wherein the one or more sleep-related parameters include an apnea-hypopnea index (AHI), a number of events per hour, a pattern of events, a sleep score, a total sleep time, a total time in bed, a wake-up time, a rising time, a hypnogram, a total light sleep time, a total deep sleep time, a total REM sleep time, a number of awakenings, a sleep-onset latency, or any combination thereof.

7. The method of claim 1, wherein the selected apnea event is an apnea, a central apnea, an obstructive apnea, a mixed apnea, or a hypopnea.

8. The method of claim 1, wherein the one or more sensors include a microphone, an acoustic sensor, an RF sensor, a pressure sensor, a motion sensor, a flow rate sensor, or any combination thereof.

9. The method of claim 1, wherein the user device is a smartphone, a tablet, a laptop, a television, a wearable device, a smart mirror, or a respiratory therapy device.

10. The method of claim 1, further comprising:

identifying, based at least in part on the data, a second plurality of events experienced by the user during the sleep session;

selecting a second apnea event from the second plurality of events; and causing to be communicated to the user via the user device a second event indication that aids in identifying the second apnea event within the graphical representation of the portion of the respiration signal.

11. The method of claim 1, wherein the portion of the respiration signal is associated with one of (a) about 3 minutes of the sleep session or (b) between about 20 seconds and about 10 minutes of the sleep session.

12. The method of claim 1, wherein the selecting the apnea event from the plurality of events includes using a linear regression algorithm.

13. The method of claim 1, wherein the selecting the apnea event from the plurality of events includes analyzing the data to identify (i) one or more breathing pauses of the user during the sleep session, (ii) a frequency of the one or more sounds in the audio data during the sleep session, (iii) a change in frequency of the one or more sounds in the audio data during the sleep session, (iv) an amplitude of the one or more sounds in the audio data during the sleep session, (v) a change in amplitude of the one or more sounds in the audio data during the sleep session, or (vi) any combination thereof.

14. The method of claim 13, wherein the apnea event selected from the plurality of events is associated with one selected from the group consisting of: (a) a breathing pause that is greater than a breathing pause for each of the other ones of the plurality of events, (b) a change in audio frequency that is greater than a change in audio frequency for each of the other ones of the plurality of events, (c) a change in audio amplitude that is greater than a change in audio amplitude for each of the other ones of the plurality of events, and (d) a pattern of changes in audio amplitude.

15. The method of claim 1, wherein the at least a portion of the data for determining the respiration signal includes at least a portion of the respiration data.

16. The method of claim 15, wherein the at least a portion of the data for determining the respiration signal also includes at least a portion of the audio data.

17. The method of claim 1, wherein the event indication comprises information associated with the selected apnea event overlaid within the graphical representation of the portion of the respiration signal; and wherein the causing the portion of the audio data associated with the selected apnea event to be communicated to the user via the user device is in response to a selection of the playback bar.

18. A system comprising:

a memory storing machine-readable instructions; and a control system including one or more processors configured to execute the machine-readable instructions to:

receive data associated with a sleep session of a user, the data including (i) respiration data associated with the user during at least a portion of the sleep session and (ii) audio data reproducible as one or more sounds associated with the user during at least a portion of the sleep session;

determine a respiration signal associated with the user during the sleep session based, at least in part, on at least a portion of the data;

identify a plurality of events experienced by the user during the sleep session based, at least in part, on at least a portion of the data;

select an apnea event from the plurality of events;

cause a portion of the audio data associated with the selected apnea event to be communicated to the user via a user device; and cause to be communicated to the user via the user device (i) a graphical representation of a portion of the respiration signal, (ii) an event indication that aids in identifying the selected apnea event within the graphical representation of the portion of the respiration signal, and (iii) a playback bar that is time-synchronized to the graphical representation of the portion of the respiration signal, wherein the playback bar traverses the graphical representation along a time axis of the respiration signal to indicate a start, a duration, and an end of the selected apnea event, thereby co-registering playback progress of the portion of the audio data with a temporal extent of the selected apnea event within the graphical representation of the portion of the respiration signal.

19. The system of claim 18, further comprising:

a respiratory therapy system including:

a respiratory therapy device configured to supply pressurized air; and an interface coupled to the respiratory device via a conduit, the interface being configured to engage a user and aid in directing the supplied pressurized air to an airway of the user.

20. The system of claim 19, wherein a first one of the one or more sensors is coupled to or integrated in a portion of the respiratory therapy system.

21. The system of claim 20, wherein a second one of the one or more sensors is coupled to or integrated in the user device, wherein the first sensor is configured to generate the respiration data and the second sensor is configured to generate the audio data.

22. The system of claim 18, wherein the event indication comprises information associated with the selected apnea event overlaid within the graphical representation of the portion of the respiration signal; and wherein the portion of the audio data associated with the selected apnea event is caused to be communicated to the user via the user device in response to a selection of the playback bar.

* * * * *